US007664606B2

(12) United States Patent
Suzuki et al.

(10) Patent No.: US 7,664,606 B2
(45) Date of Patent: Feb. 16, 2010

(54) APPARATUS AND METHOD FOR MONITORING BIOLOGICAL INFORMATION, AND COMPUTER PROGRAM PRODUCT

(75) Inventors: Takuji Suzuki, Kanagawa (JP); Kazushige Ouchi, Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 203 days.

(21) Appl. No.: 11/689,126

(22) Filed: Mar. 21, 2007

(65) Prior Publication Data
US 2008/0004811 A1 Jan. 3, 2008

(30) Foreign Application Priority Data
Jun. 28, 2006 (JP) ............... 2006-178644

(51) Int. Cl.
*G01N 33/48* (2006.01)
*G06F 19/00* (2006.01)
(52) U.S. Cl. ...................................................... 702/19
(58) Field of Classification Search .................. 702/19, 702/127, 72, 79, 176, 182, 183, 189; 600/301, 600/481, 500, 502, 509
See application file for complete search history.

(56) References Cited

U.S. PATENT DOCUMENTS

| 5,902,250 | A * | 5/1999 | Verrier et al. | 600/515 |
|---|---|---|---|---|
| 2005/0143665 | A1 * | 6/2005 | Huiku et al. | 600/500 |
| 2005/0187480 | A1 * | 8/2005 | Kario et al. | 600/483 |
| 2005/0234314 | A1 * | 10/2005 | Suzuki et al. | 600/301 |
| 2006/0094967 | A1 * | 5/2006 | Bennett et al. | 600/508 |
| 2006/0189855 | A1 * | 8/2006 | Moriya et al. | 600/301 |
| 2006/0200011 | A1 * | 9/2006 | Suzuki et al. | 600/301 |
| 2006/0224074 | A1 * | 10/2006 | Ouchi et al. | 600/513 |
| 2006/0241359 | A1 * | 10/2006 | Nagai et al. | 600/301 |
| 2007/0021673 | A1 * | 1/2007 | Arbel et al. | 600/500 |
| 2007/0083125 | A1 | 4/2007 | Ouchi et al. | |
| 2007/0106183 | A1 * | 5/2007 | Suzuki et al. | 600/595 |
| 2007/0123787 | A1 * | 5/2007 | Kitajima et al. | 600/509 |
| 2008/0004811 | A1 | 1/2008 | Suzuki et al. | |
| 2008/0076978 | A1 | 3/2008 | Ouchi et al. | |
| 2008/0242956 | A1 | 10/2008 | Suzuki et al. | |

FOREIGN PATENT DOCUMENTS

| JP | 3-272745 | 12/1991 |
|---|---|---|
| JP | 4-183439 | 6/1992 |
| JP | 5-56902 | 8/1993 |
| JP | 8-117198 | 5/1996 |

(Continued)

OTHER PUBLICATIONS

U.S. Appl. No. 12/212,182, filed Jun. 20, 2007, Suzuki.

*Primary Examiner*—Michael P. Nghiem
*Assistant Examiner*—Cindy H Khuu
(74) *Attorney, Agent, or Firm*—Oblon, Spivak, McClelland, Maier & Neustadt, L.L.P.

(57) ABSTRACT

A biological-information monitoring apparatus includes a detecting unit that detects pulse intervals of a target person. Moreover, a first calculating unit calculates an average pulse interval that is an average of the pulse intervals within a first period. The first period is decided based on a target pulse interval. Finally, a second calculating unit calculates a parasympathetic nervous index based on a difference between the average pulse interval and the target pulse interval.

11 Claims, 20 Drawing Sheets

FOREIGN PATENT DOCUMENTS

| | | |
|---|---|---|
| JP | 2002-306455 | 10/2002 |
| JP | 2003-532456 | 11/2003 |
| JP | 2004-305258 | 11/2004 |
| JP | 3643564 | 2/2005 |
| JP | 2005-279113 | 10/2005 |
| JP | 2005-304942 | 11/2005 |
| JP | 2005-319256 | 11/2005 |
| JP | 2006-26302 | 2/2006 |
| JP | 2006-34803 | 2/2006 |

* cited by examiner

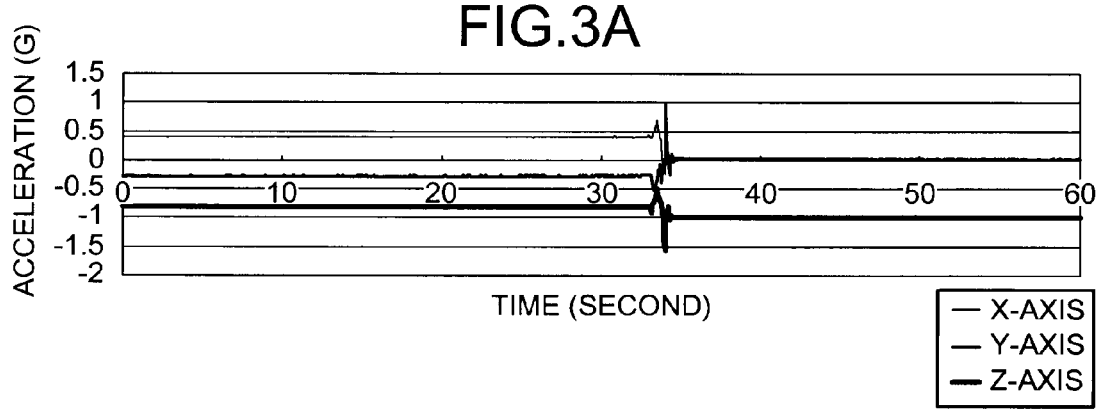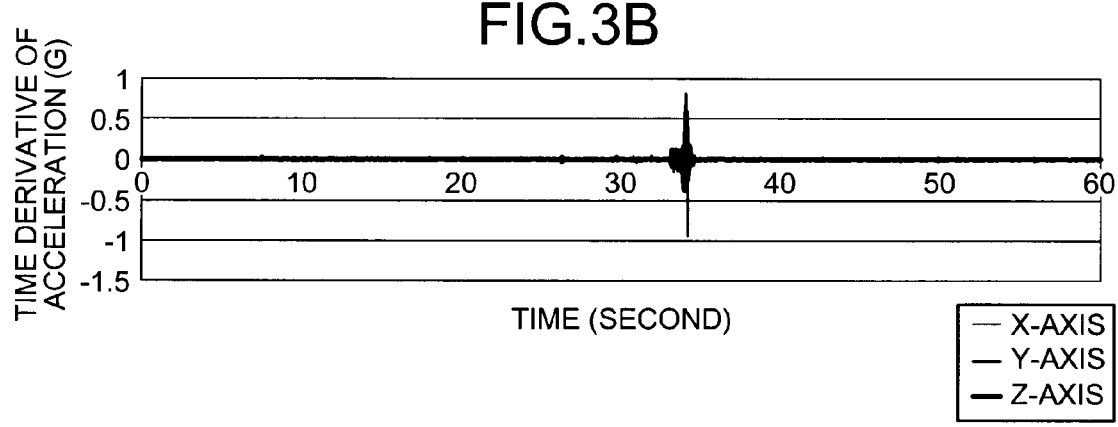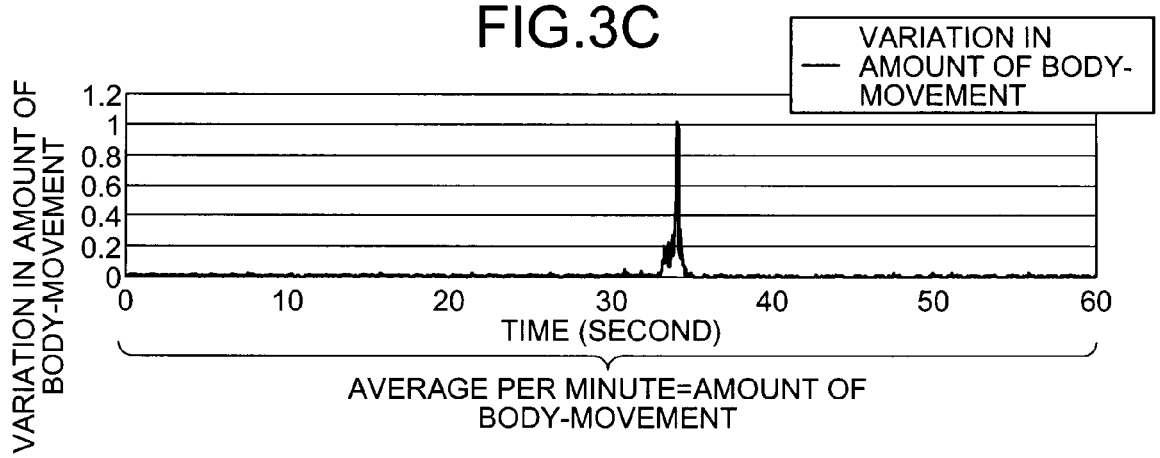

APPARATUS AND METHOD FOR MONITORING BIOLOGICAL INFORMATION, AND COMPUTER PROGRAM PRODUCT

CROSS-REFERENCE TO RELATED APPLICATIONS

This application is based upon and claims the benefit of priority from the prior Japanese Patent Application No. 2006-178644, filed on Jun. 28, 2006; the entire contents of which are incorporated herein by reference.

BACKGROUND OF THE INVENTION

1. Field of the Invention

The present invention relates to an apparatus, a method, and a computer program product for monitoring biological information of a target person.

2. Description of the Related Art

Various methods are known for monitoring autonomic-nervous activity of living beings such as a person. Recently, the frequency-analysis method is being commonly used. In the frequency-analysis method, levels of sympathetic and parasympathetic nervous activities are calculated by analyzing fluctuations in the heartbeat intervals.

A heart rate of a person is usually calculated from peak-to-peak intervals in a waveform obtained from an electrocardiogram, a photoelectric, or pressure-type of sphygmograph of the person. A peak appears in the waveform due to a heartbeat. In the frequency-analysis method, a series of data on heartbeat intervals are collected, the data are converted into a frequency spectrum, and powers of a low-frequency band (LF: a band ranging from 0.05 hertz to 0.15 hertz) and a high-frequency band (HF: a band ranging from 0.15 hertz to 0.4 hertz) in the spectrum are determined as the heart rate. In this manner, the frequency-analysis method makes use of the relation between the LF and the HF and the autonomic-nervous activity.

The frequency-analysis method, however, requires high-end computer environment, which is not always available. If such a computer environment is not available, one approach to analyze the frequency is to use indexes such as the RR50 and the mean of the sum of the squared differences in successive R-R intervals (MSSD).

The RR50 is an index that is obtained as follows. That is, difference between intervals of two adjacent heartbeats is calculated for all the heartbeats in a predetermined period, for example, 1 minute, and the RR50 is the number of heartbeats for which the difference exceeds 50 milliseconds.

On the other hands, the MSSD is an index that is obtained as follows. That is, square of difference between intervals of two adjacent heartbeats is calculated for all the heartbeats in a predetermined period, and the MSSD is the average of the squares. Both the RR50 and the MSSD have been used to monitor autonomic-nervous activity and they make use of degree of fluctuation in the heartbeat intervals.

Autonomic-nervous activity can be monitored with even other techniques. There is known a method of evaluating a parasympathetic-nervous activity in real time based on an electrocardiogram and a breathing patter of a person (see JP-A 2005-319256 (KOKAI)). On the other hand, there is known a method of evaluating parasympathetic-nervous activity based on magnitude variation among the last three data of the heart-rate intervals of a person (see JP-A H8-117198 (KOKAI)).

A person's emotional status, that is, whether the person is feeling stress, can be determined by monitoring the autonomic-nervous activity. Moreover, this technique can be effectively used to prevent a person from snoozing when he/she is determined to be sleepy, and determine a state of sleep based on a changing pattern of the autonomic-nervous activity. This technique can be used even for medical purposes. For example, JP-A No. 3643564 (KOKAI) discloses a technique in which an autonomic-nervous function is evaluated based on a fluctuation of the heart rate, and changes of the heart rate is monitored before and after a blood vessel gets compressed due to a cuff during a blood-pressure measurement.

However, the conventional frequency-analysis method involves a large amount of calculations so that this method cannot be realized on low-end computer systems that are generally incorporated in mobile devices. On the other hand, high-end computers systems are expensive and require high-power batteries, which adds to the cost.

With regard to the RR50 and the MSSD indexes, the result includes both low-frequency components (equivalent to the LF) and high-frequency components (equivalent to the HF) those are a part of fluctuation components so that it is difficult to separate the result into those for sympathetic nerve and those for parasympathetic nerve.

The technique disclosed in the JP-A 2005-319256 (KOKAI) has a disadvantage that signals from two pieces of information are required, i.e., the electrocardiogram and the breathing pattern, so that the structure of the overall system becomes complicated.

The technique disclosed in the JP-A H8-117198 (KOKAI) has a disadvantage that because the evaluation is made based on the number of predetermined patterns of last three data, for example, "large, small, large", or "small, large, small", the evaluation is not quantitative.

SUMMARY OF THE INVENTION

According to an aspect of the present invention, a biological-information monitoring apparatus includes a detecting unit that detects pulse intervals of a target person; a first calculating unit that calculates an average pulse interval that is an average of the pulse intervals within a first period that is decided based on a target pulse interval; and a second calculating unit that calculates a parasympathetic nervous index based on a difference between the average pulse interval and the target pulse interval.

According to another aspect of the present invention, a biological-information monitoring apparatus includes a detecting unit that detects pulse intervals of a target person; a first calculating unit that calculates an average pulse interval that is an average of the pulse intervals within a first period that is decided based on a target pulse interval; and a second calculating unit that calculates a sympathetic nervous index based on a degree of dispersion of the average pulse intervals within a second period.

According to still another aspect of the present invention, a biological-information monitoring apparatus includes a monitoring unit that monitors a pulse amplitude of a target person; and a calculating unit that calculates a sympathetic nervous index based on the pulse amplitude monitored by the monitoring unit.

According to still another aspect of the present invention, a method of monitoring and processing biological information of a target person includes detecting pulse intervals of the target person; calculating an average pulse interval that is an average of the pulse intervals within a first period that is decided based on a target pulse interval; and calculating a parasympathetic nervous index based on a difference between the average pulse interval and the target pulse interval.

According to still another aspect of the present invention, a computer product including a recording medium readable by a computer and containing a plurality of instructions executable on the computer for monitoring and processing of biological information, the instructions causing the computer to execute detecting pulse intervals of a target person; calculating an average pulse interval that is an average of the pulse intervals within a first period that is decided based on a target pulse interval; and calculating a parasympathetic nervous index based on a difference between the average pulse interval and the target pulse interval.

BRIEF DESCRIPTION OF THE DRAWINGS

FIG. 3A is a graph of acceleration data in three perpendicular directions;

FIG. 3B is a graph of time derivatives of accelerations in the three directions within 1 minute;

FIG. 3C is a graph of variations in amount of body-movements within 1 minute;

DETAILED DESCRIPTION OF THE INVENTION

Exemplary embodiments according to the present invention will be explained below with reference to the accompanying drawings.

Figure 1:
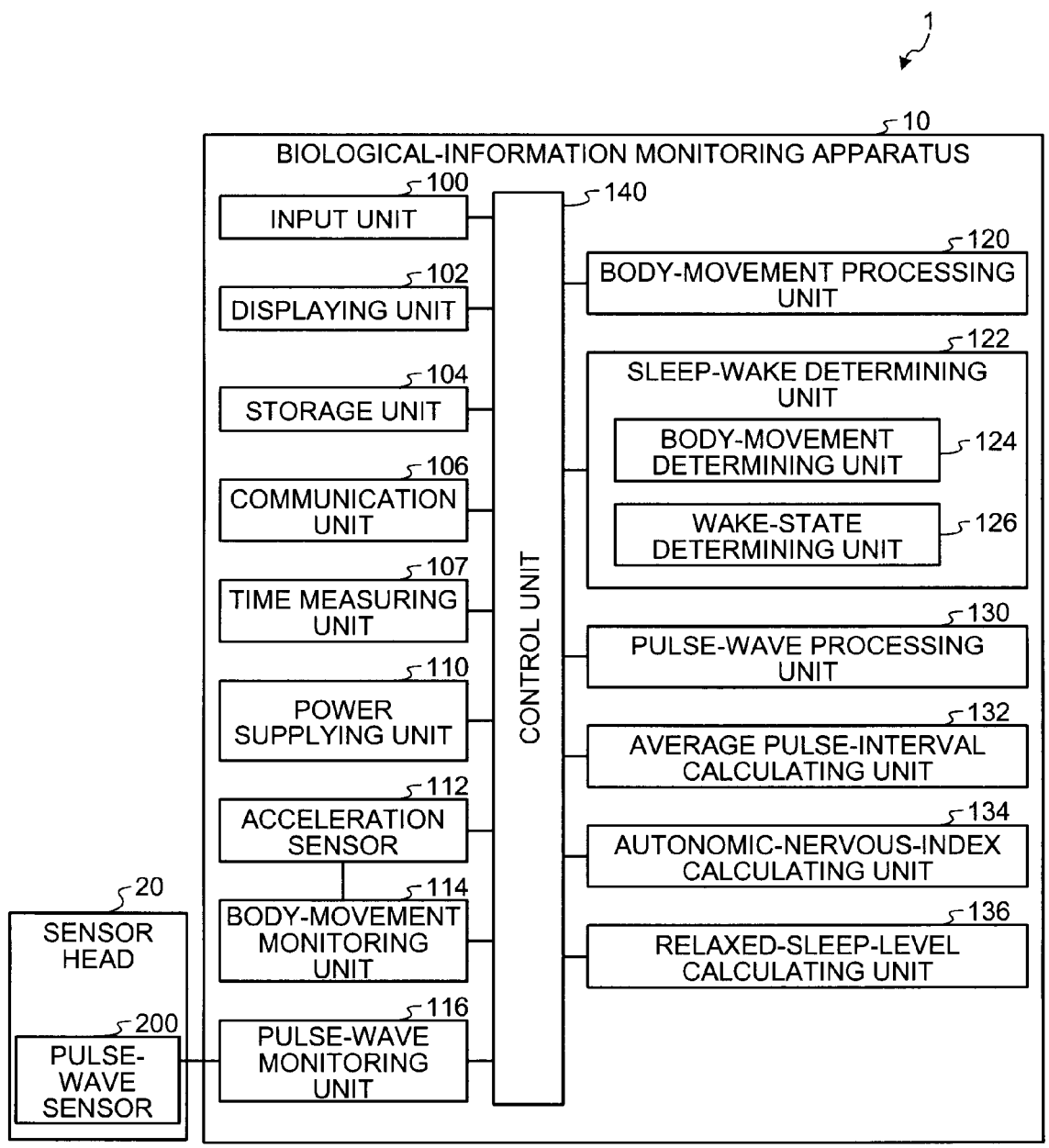
FIG. 1 is a block diagram of a biological-information monitoring system according to a first embodiment of the present invention.

As shown in FIG. 1, a biological-information monitoring system 1 according to a first embodiment of the present invention includes a biological-information monitoring apparatus 10 and a sensor head 20. The sensor head 20 is a sensor module that can be attached to a body part of a target person such as a finger (see FIG. 2). The sensor head 20 includes a pulse-wave sensor 200 that detects a pulse wave of the target person.

The biological-information monitoring apparatus 10 monitors biological information based on the pulse wave detected by the sensor head 20. The biological information represents an index of the autonomic nerve. The autonomic nerve can be the sympathetic nerves or the parasympathetic nerves in the human body. The biological-information monitoring apparatus 10 includes an input unit 100, a displaying unit 102, a storage unit 104, a communication unit 106, a time measuring unit 107, a power supplying unit 110, an acceleration sensor 112, a body-movement monitoring unit 114, a pulse-wave monitoring unit 116, a body-movement processing unit 120, a sleep-wake determining unit 122, a pulse-wave processing unit 130, an average pulse-interval calculating unit 132, an autonomic-nervous-index calculating unit 134, a relaxed-sleep-level calculating unit 136, and a control unit 140. The sleep-wake determining unit 122 includes a body-movement determining unit 124 and a wake-state determining unit 126.

Figure 2:
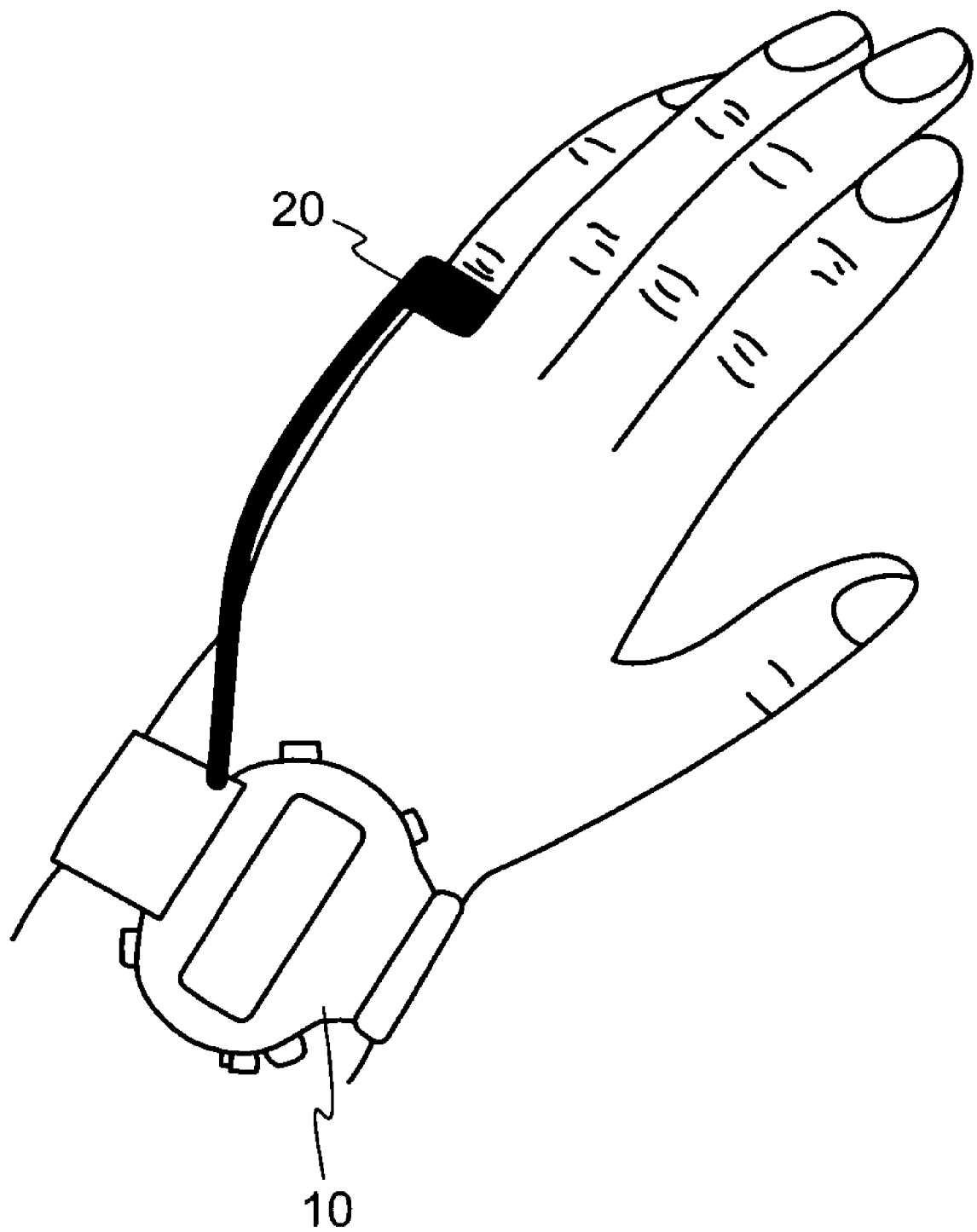
FIG. 2 is a schematic for explaining attachment of the biological-information monitoring system to a hand of a target person.

As shown in FIG. 2, the sensor head 20 can be attached to a finger of the target person, and the biological-information monitoring apparatus 10 can be attached to a wrist of the target person like a wristwatch. Alternatively, the sensor head 20 can be attached to a palm of the target person with an adhesive plaster.

The input unit 100 is a switch, which is operated by the target person, to turn ON or OFF of power of the biological-information monitoring apparatus 10. The input unit 100 is operated to change the display screens displayed on the displaying unit 102. The displaying unit 102, which can be a liquid crystal display (LCD), displays the result of monitoring of the biological information. The storage unit 104, which can be a flash memory, stores therein data. The data can be monitored data such as pulse waves and body movements, processed data such as pulse intervals, and the various thresholds used for determining a sleep state.

The communication unit 106, which can be the Bluetooth, interacts with devices such as a personal computer (not shown), a Personal Digital Assistants (PDA) terminal (not shown), or a cellular phone for data communications (not shown). The time measuring unit 107, which can be a real-time clock, measures time. The power supplying unit 110, which can be a battery, supplies power to the biological-information monitoring apparatus 10.

The acceleration sensor 112 measures accelerations of the target person as body-movement data. The acceleration sensor 112 includes sensors that can measure the body-movement data in three perpendicular directions (X, Y, and Z) in the range from −2 g to 2 g. The body-movement monitoring unit 114 includes an adjusting circuit that adjusts gains and offsets of the analog data obtained by the acceleration sensor 112, and a 10-bit Analog-to-Digital Converter (ADC) that converts the analog data into digital data. The body-movement monitoring unit 114 inputs the digital data as the acceleration data into the control unit 140.

The body-movement processing unit 120 calculates a time derivative of the acceleration data in each of the three directions by differentiating the acceleration data with respect to time. Moreover, the body-movement processing unit 120 calculates a variation in body-movement, which is a root-sum-square value of the time derivative of the acceleration in the three directions. Furthermore, the body-movement processing unit 120 calculates an amount of body-movement, which is the average amount of the variations of body movement at the pulse interval. The variation in body-movement and the amount of body-movement are sent to the body-movement determining unit 124 for body-movement determination.

The variation in body movement represents, for example, a variation of the target person's body movements for every 50 milliseconds. Moreover, the amount of body movement represents, for example, the average of the variation of body movement for every 1 minute.

FIG. 3A is a graph of acceleration data in the three directions, FIG. 3B is a graph of time derivatives of accelerations in the three directions, and FIG. 3C is a graph of variations in amount of body-movements in 1 minute. The body-movement processing unit 120 calculates the acceleration data in the three directions from the measurement of body-movement by the body-movement monitoring unit 114. The body-movement processing unit 120 also calculates a time derivative of the accelerations in the three directions for a period of 1 minute. Finally, the body-movement processing unit 120 calculates the variation in body-movement obtained from the time derivatives of the accelerations. Namely, the variation in body-movement is calculated from the acceleration data, and the amount of body movement is calculated by averaging the variation in body-movement.

The sleep-wake determining unit 122 determines whether the target person is in a wake state or a sleep state based on the body-movement data. The body-movement determining unit 124 of the sleep-wake determining unit 122 determines a movement of the target person as the body movement when the variation in body-movement is larger than a body-movement threshold. The body-movement threshold is set to, for example, 0.01 G, which is the minimum value used in a body-movement measuring device.

When the frequency of body movements determined by the body-movement determining unit 124 is equal to or larger than a frequency threshold, the wake-state determining unit 126 determines that the body movement has occurred during the wake state. When the frequency is under the frequency threshold, the wake-state determining unit 126 of the sleep-wake determining unit 122 determines that the body movement has occurred during the sleep state. Furthermore, when the frequency is equal to or larger than the frequency threshold and the pulse interval is shorter than the average of past pulse intervals in the sleep state, the wake-state determining unit 126 determines that the body movement has occurred during the wake state. The frequency threshold is, for example, 20 times/minute based on past frequency data of body movements in the wake state.

Figure 4:
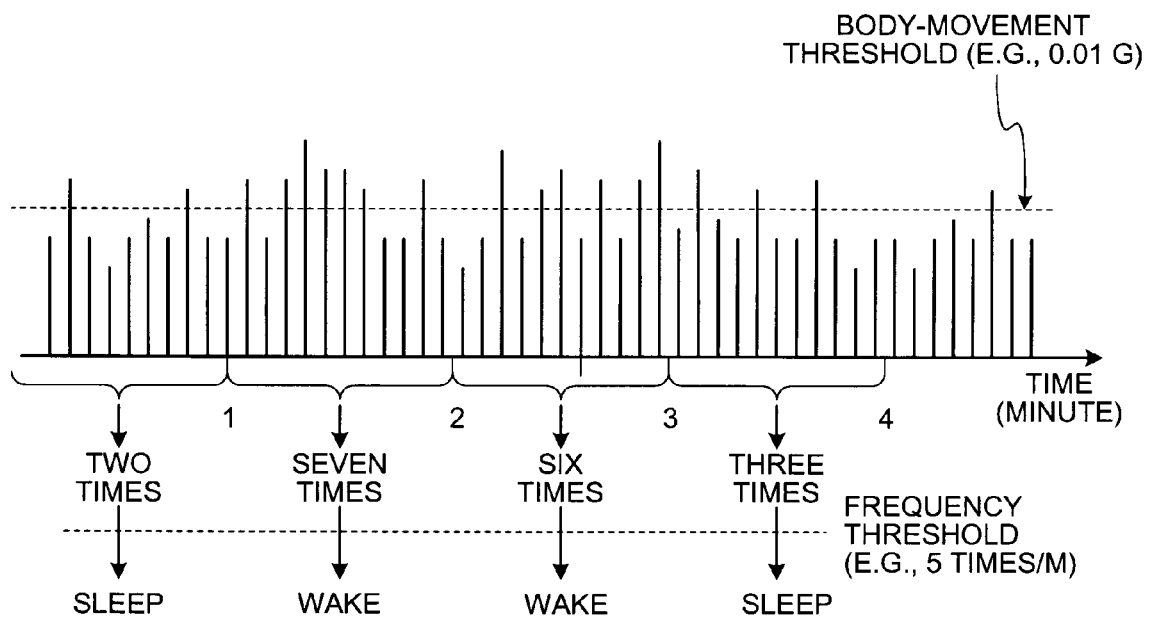
FIG. 4 is a schematic for explaining processes performed by a body-movement determining unit and a wake-state determining unit shown in FIG. 1.

As shown in FIG. 4, the body-movement threshold can be set to 0.01 G, and the body-movement frequency can be set to 5 times/minute. When those values are set, the body-movement determining unit 124 determines only a body-movement that is equal to or larger than 0.01 G as the body movement. The wake-state determining unit 126 determines, when the frequency of body movements is 2 times/minute or 3 times/minute, that the body movement has occurred during the wake state, and when the frequency is 6 times/minute or 7 times/minute, determines that the body movement has occurred during the sleep state.

The pulse-wave sensor 200 is made up of, for example, a blue light-emitting diode (LED) (not shown) and a photodiode (not shown). The LED illuminates a light on the surface of the finger of the target person, and the photodiode collects the light reflected from the surface of the finger. A pulse wave can be obtained from the variations in the light captured by the photodiode. These variations depend on the variations in the blood-flow in the blood capillaries in the finger. The photodiode outputs a current that represents the amount of light to the pulse-wave monitoring unit 116.

The pulse-wave monitoring unit 116 includes a current-to-voltage converter (not shown), an amplifier (not shown), a high-pass filter (HPF) (of cut-off frequency 0.1 hertz) (not shown) and a low-pass filter (LPF) (of cut-off frequency 50 hertz) (not shown), and a 10-bit ADC (not shown). The current-to-voltage converter converts the current into a voltage, the amplifier amplifies the voltage, the HPF and the LPF perform filtering of the voltage, and the 10-bit ADC converts the voltage into digital data. The pulse-wave monitoring unit 116 inputs the digital pulse-wave data into the control unit 140.

Figure 5:
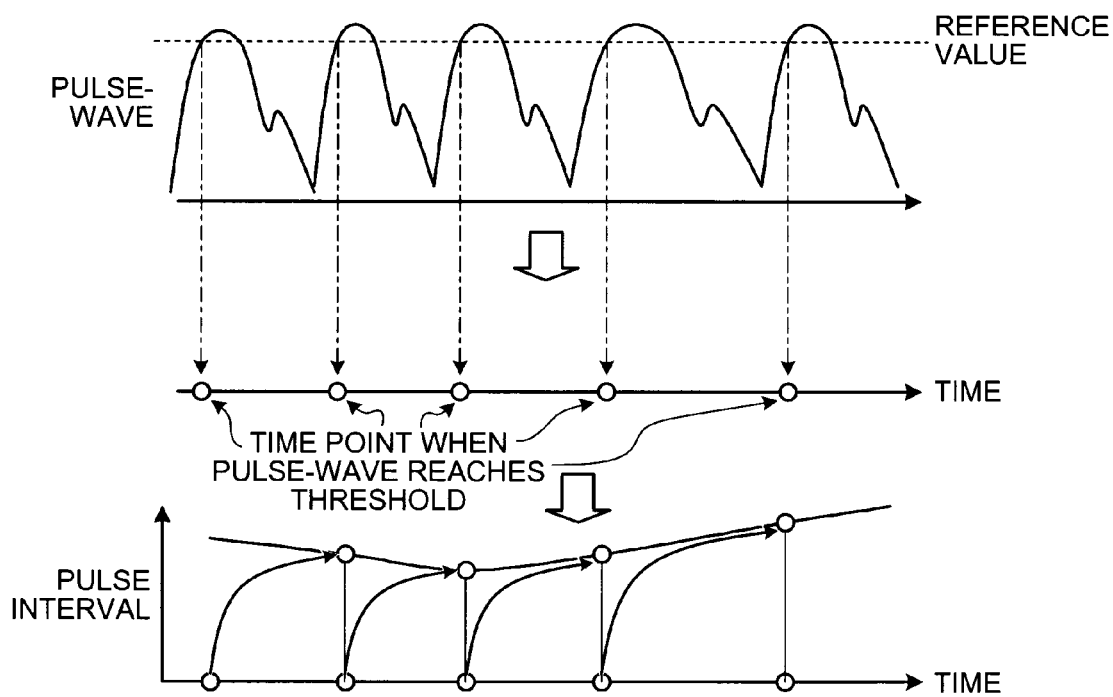
FIG. 5 is a schematic for explaining a process of calculating pulse-interval data.

The pulse-wave processing unit 130 obtains pulse intervals data by sampling the pulse-wave data. More specifically, as shown in FIG. 5, the pulse-wave processing unit 130 samples the pulse-wave data, and obtains the maximum and minimum values of the pulse-wave data within about one second before and after a processing point in the sampled pulse-wave data. A predetermined value between the maximum value and the minimum value is defined as a reference value. Assuming the difference between the maximum value and the minimum value to be an amplitude value, the reference value can be set to 90% of the amplitude value from the minimum value.

Next, out of the series of the pulse-wave data excluding components of direct current variation, points of time when the pulse wave reaches the reference value (for example, a point before the peak) are calculated. Alternately, a point after the peak can be counted. Pulse interval data is obtained from each interval between the calculated points of time. The pulse-interval data is stored in the storage unit 104. The pulse-interval data is discarded if it is at the same timing as the timing on which the body-movement determining unit 124 determines that a body movement has occurred.

Figure 6:
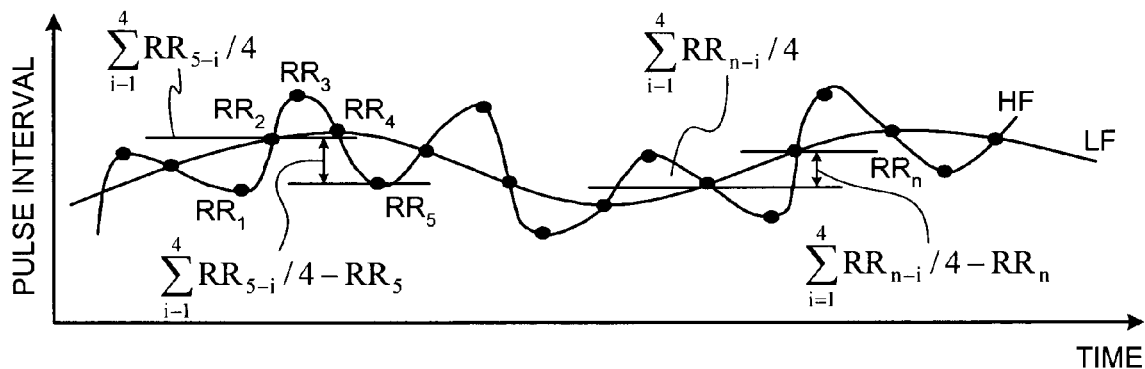
FIG. 6 is a graph for explaining operations performed by an average pulse-interval calculating unit and an autonomic-nervous-index calculating unit shown in FIG. 1.

As shown in FIG. 6, the pulse-interval data contains high-frequency fluctuation components and low-frequency fluctuation components. The average pulse-interval calculating unit 132 and the autonomic-nervous-index calculating unit 134 calculate an autonomic nervous index based on the pulse-interval data. Precisely, the HF fluctuation components and the LF fluctuation components are separated from each other, and the HF fluctuation components and the LF fluctuation components are respectively regarded as a parasympathetic nervous index and a sympathetic nervous index.

The average pulse-interval calculating unit 132 calculates the average of the pulse-interval data within a predetermined range, i.e., the average pulse interval. The autonomic-nervous-index calculating unit 134 calculates an autonomic nervous index based on the average pulse interval.

Every time pulse-interval data is newly obtained, the average pulse-interval calculating unit 132 reads the predetermined number of the past pulse-interval data excluding the obtained latest data from the storage unit 104. It is assume that RR5 is the latest obtained data and the average pulse-interval calculating unit 132 reads data on the past pulse intervals from RR1 to RR4. In other words, a period from RR1 to RR4 is a monitoring period.

The average pulse-interval calculating unit 132 calculates "av", which is an average of data on the past four points of pulse intervals, i.e., the average pulse interval, with Equation 1. In Equation 1, "i" represents the number of the past data.

$$av = \sum_{i=1}^{4} RR_{5-i}/4 \quad (1)$$

The autonomic-nervous-index calculating unit 134 squares a difference between the average pulse interval and the latest pulse interval (RR5) as shown in Equation 2, and stores a result in the storage unit 104.

$$\left(\sum_{i=1}^{4} RR_{5-i}/4 - RR_5\right)^2 \quad (2)$$

Next, the autonomic-nervous-index calculating unit 134 calculates the average of the squared differences of pulse-interval data at a predetermined interval, for example, per minute, as shown in Equation 3, and stores the average in the storage unit 104. The average is defined as a parasympathetic nervous index, so-called an averaged MSSD (aMSSD). In Equation 3, "N" represents the number of the pulse-interval data obtained in 1 minute, "i" represents a value added one with the number of the past pulse-interval data, and "RRi" represents the latest pulse-interval data.

$$aMSSD = \sum_{i=4-N}^{N} \left(\sum_{j=i-3}^{i} RR_{j-1}/4 - RR_i\right)^2 / N \times 100 \quad (3)$$

Thus, the aMSSD, which is the parasympathetic nervous index, can be accurately calculated with an easy operation. Because of a low amount of transactions, this operation can be realized on even low-end mobile devices such as wristwatches.

Although the number of the past pulse-interval data is defined as four in the embodiment, the number can be changed depending on, for example, a breathing cycle or a heart-rate cycle. It has been known that a cycle of HF components is synchronized with the breathing cycle with respect to a physiological mechanism. The breathing cycle is generally from 15 beats/minute to 20 beats/minute, and the heart-rate cycle is about 60 beats/minute. The number of the past pulse intervals, i.e., a count for a moving average, can be defined based on a ratio between the breathing cycle and the heart-rate cycle. For example, from three to five are obtained based on the breathing cycle, although the calculated number varies from person to person as the target person. Therefore, it is recommended to monitor the ratio between the breathing cycle and the heart rate for each target person to set a suitable value if the device is shared by many persons.

When only the breathing cycle have been calculated in advance, the number of the past pulse intervals can be defined based on the breathing cycle. In other words, the range of the moving average can be dynamically changed in response to the breathing cycle. To dynamically change the population, a total value of pulse intervals within the expected number of the population (e.g., from three to five) is calculated, and out of the totals a value nearest to a specified breathing cycle is employed.

Although Equations 1 to 3 assume that the number of the past pulse intervals is four, the number need not be four. When the number of the past pulse intervals is "n", the aMSSD is calculated with Equation 4.

$$aMSSD = \sum_{i=n-N}^{N} \left(\sum_{j=i-n+1}^{i} RR_{j-1}/n - RR_i\right)^2 / N \times 100 \quad (4)$$

Figure 7:
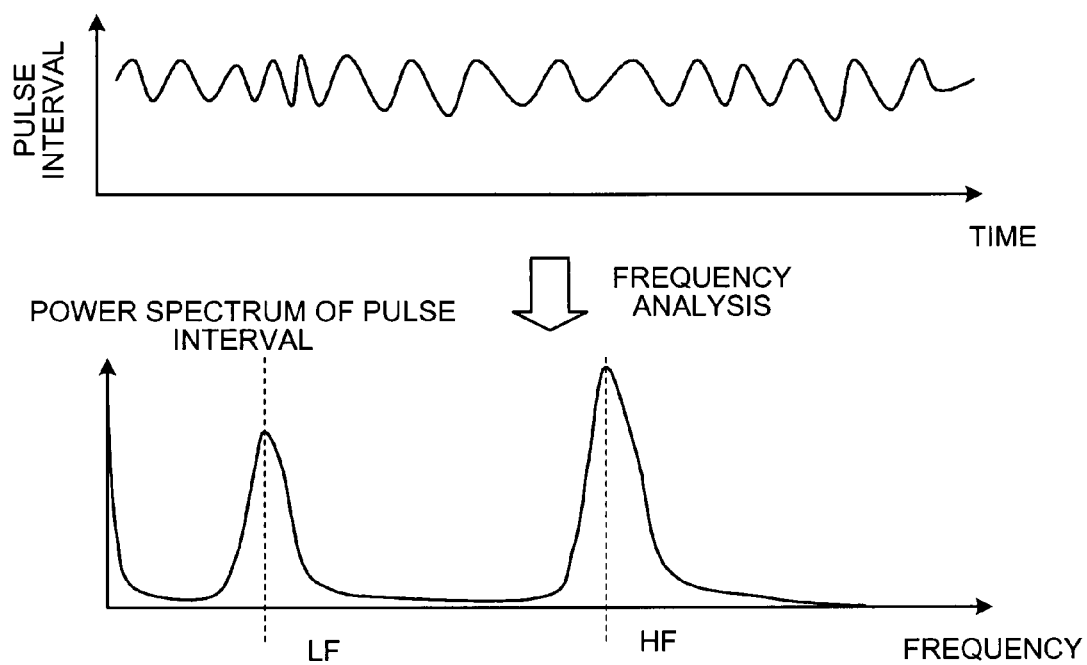
FIG. 7 is a graph for explaining low-frequency components and high-frequency components contained in the pulse-interval data.

As shown in FIG. 7, two autonomic nervous indexes, an LF index for the LF area (about from 0.05 hertz to 0.15 hertz) and an HF index for the HF area (about from 0.15 hertz to 0.4 hertz), are obtained based on a frequency spectrum of the pulse-interval data obtained by the analyzing method such as the Fast Fourier Transform (FFT). The LF index represents the sympathetic nervous index, and the HF index represents the parasympathetic nervous index.

When the conventional MSSD, which is used to calculate the parasympathetic nervous index corresponding to an index for the HF area, is employed, the result contains fluctuation components of both the LF and the HF, so that it is difficult to separate only the HF fluctuation components.

When the aMSSD according to the embodiments of the present invention is employed, only the HF components can be selectively extracted from the components containing both the HF and LF components shown in FIG. 7. Therefore, the result obtained from the aMSSD is more accurate than that obtained from the conventional MSSD.

Figure 8:
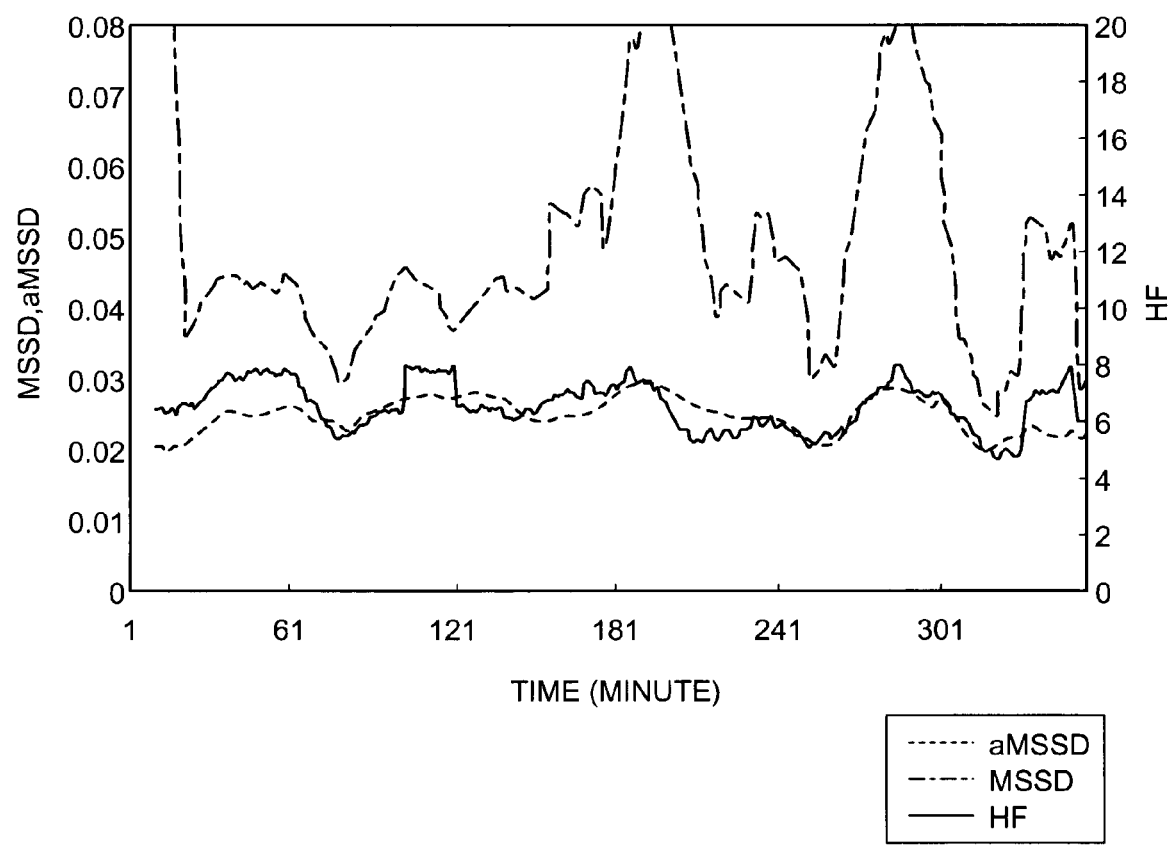
FIG. 8 is a graph of aMSSDs.
Figure 9:
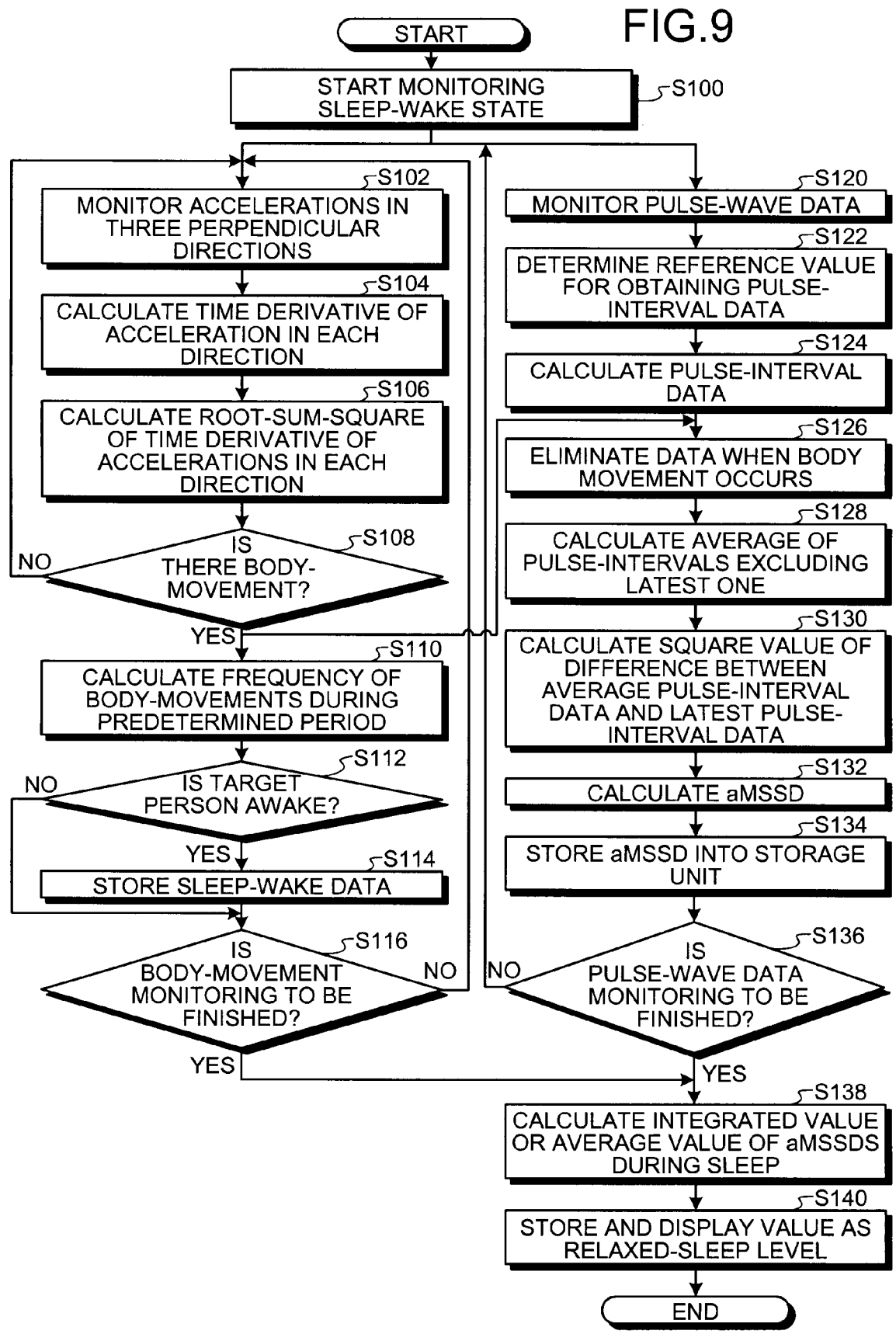
FIG. 9 is a flowchart for explaining operations performed by a biological-information monitoring apparatus shown in FIG. 1.

FIG. 8 is a graph for explaining the HF of parasympathetic nervous index, and results obtained with the MSSD and the aMSSD, respectively. It can be seen that curve for the MSSD largely deviates from that of the HF, while the curve for the aMSSD almost matches with that of the HF. An average correlation coefficient of ten data showed an improvement 0.38 to 0.67.

The relaxed-sleep-level calculating unit 136 calculates an integrated value or an average value of the aMSSD in the sleep state stored in the storage unit 104 as the autonomic nervous index, and inputs the integrated value or the average value into the storage unit 104 as a relaxed-sleep level. Moreover, the displaying unit 102 displays the integrated value or the average value.

The control unit 140 controls the biological-information monitoring apparatus 10 based on the requests and the instructions received from the target person. For example, the control unit 140 controls operations such as power ON or OFF, and calculation and displaying of the relaxed-sleep level in response to the target person's instruction.

The target person wears the biological-information monitoring system 1 before sleeping, and turns the power ON by operating the input unit 100. As a result, the biological-information monitoring system 1 starts monitoring sleep-wake state of the target person (step S100). Specifically, the acceleration sensor 112 starts monitoring the accelerations, and the pulse-wave sensor 200 starts monitoring the pulse wave data of the target person (steps S102 and S120). The acceleration sensor 112 monitors the accelerations in three perpendicular directions.

The body-movement processing unit 120 calculates a time derivative of the acceleration in the three directions by differentiating the acceleration data obtained by the body-movement monitoring unit 114 with respect to time (step S104), and calculates a root-sum-square value of the derivatives of the accelerations in the three directions (step S106). The body-movement determining unit 124 receives the root-sum-square value from the body-movement processing unit 120 and waits until another body movement takes place (step S108). When a variation of body movement, i.e., the root-sum-square value, is larger than the body-movement threshold, the movement is determined as a body movement.

When the body-movement determining unit 124 detects a body movement (Yes at step S108), the wake-state determining unit 126 calculates the frequency of body movements during a predetermined period (step S110) to determine whether the target person is in the wake-state (step S112). When the target person is determined to be in the wake-state (Yes at step S112), the wake-state determining unit 126 causes the storage unit 104 to store a time of sleep, a wake-up time, a frequency of wake state during a sleep, and an amount of body movements (step S114). When the body-movement monitoring is to be finished (Yes at step S116), the system control goes to step S138.

On the other hands, the pulse-wave processing unit 130 samples the pulse-wave data, obtains the maximum and minimum values out of a series of the sampled pulse-wave data within a predetermined period, and defines a certain value within a range between the maximum and the minimum as a reference value (step S122). The pulse-wave processing unit 130 also calculates a time when the pulse wave reaches the reference value out of the series of pulse-wave data, and obtains pulse-interval data by calculating an interval between the times (step S124). If a body movement does not occur in the period, with referring to the result by the body-movement determining unit 124, the calculated data is officially used as the pulse-interval data (step S126).

The average pulse-interval calculating unit 132 obtains the pulse-interval data with the predetermined number of past points from the storage unit 104 to calculate an average of the pulse-interval data (step S128). The autonomic-nervous-index calculating unit 134 calculates a square of a difference between the average pulse-interval data and the latest pulse-interval data (step S130), averages the squared differences within a predetermined period, for example 1 minute (step S132), i.e., calculates an aMSSD, and inputs the aMSSD into the storage unit 104 (step S134).

When the pulse-wave data monitoring is to be finished (Yes at step S136), the past aMSSD data during sleep is read from the storage unit 104 to obtain an integrated value or an average value (step S138). The integrated or average value is displayed on the displaying unit 102 as a relaxed-sleep level and stored in the storage unit 104 (step S140).

As described above, according to the biological-information monitoring apparatus 10, it is possible to calculate and the index of parasympathetic-nervous activity during the sleep. This allows easy check of sleep/wake state of a person.

Figure 10:
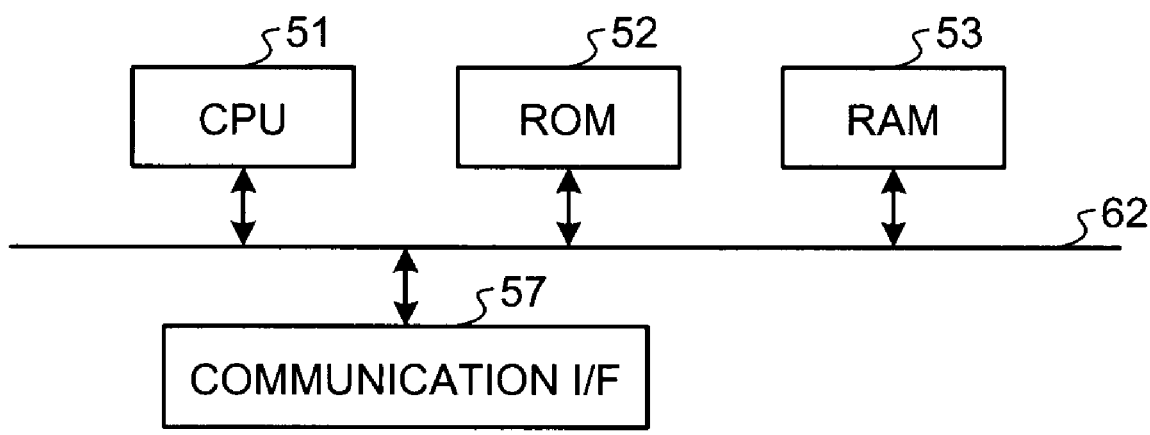
FIG. 10 is a schematic of a hardware configuration of the biological-information monitoring apparatus shown in FIG. 1.

As shown in FIG. 10, the biological-information monitoring apparatus 10 includes a read only memory (ROM) 52 for storing a computer program (hereinafter, biological-information monitoring programs) according to which the processes are performed at the body-movement processing unit 120, the sleep-wake determining unit 122, the pulse-wave processing unit 130, the average pulse-interval calculating unit 132, the autonomic-nervous-index calculating unit 134, and the relaxed-sleep-level calculating unit 136; a central processing unit (CPU) 51 for controlling each unit of the biological-information monitoring apparatus 10 according to the computer programs stored in the ROM 52; a random access memory (RAM) 53 that stores various data necessary to control the biological-information monitoring apparatus 10; a communication interface (communication I/F) 57 for connecting to a network to interact data; and a bus 62 for connecting the components to each other.

The biological-information monitoring program can also be stored, in a form of a file installable or executable on a computer, in a recording medium readable by the computer such as a compact disk read only memory (CD-ROM), a floppy disk (trademark), a digital versatile disk (DVD), or the like. The biological-information monitoring apparatus 10 reads the biological-information monitoring program from the recording medium to execute it. The biological-information monitoring program is loaded on a main storage unit to create the software units.

Alternatively, the biological-information monitoring program can be stored in another computer connected to the computer via a network such as the Internet, and downloaded to the computer via the network.

Although the invention has been described with respect to a specific embodiment, various modifications and improvements can be made to the embodiment.

Figure 11:
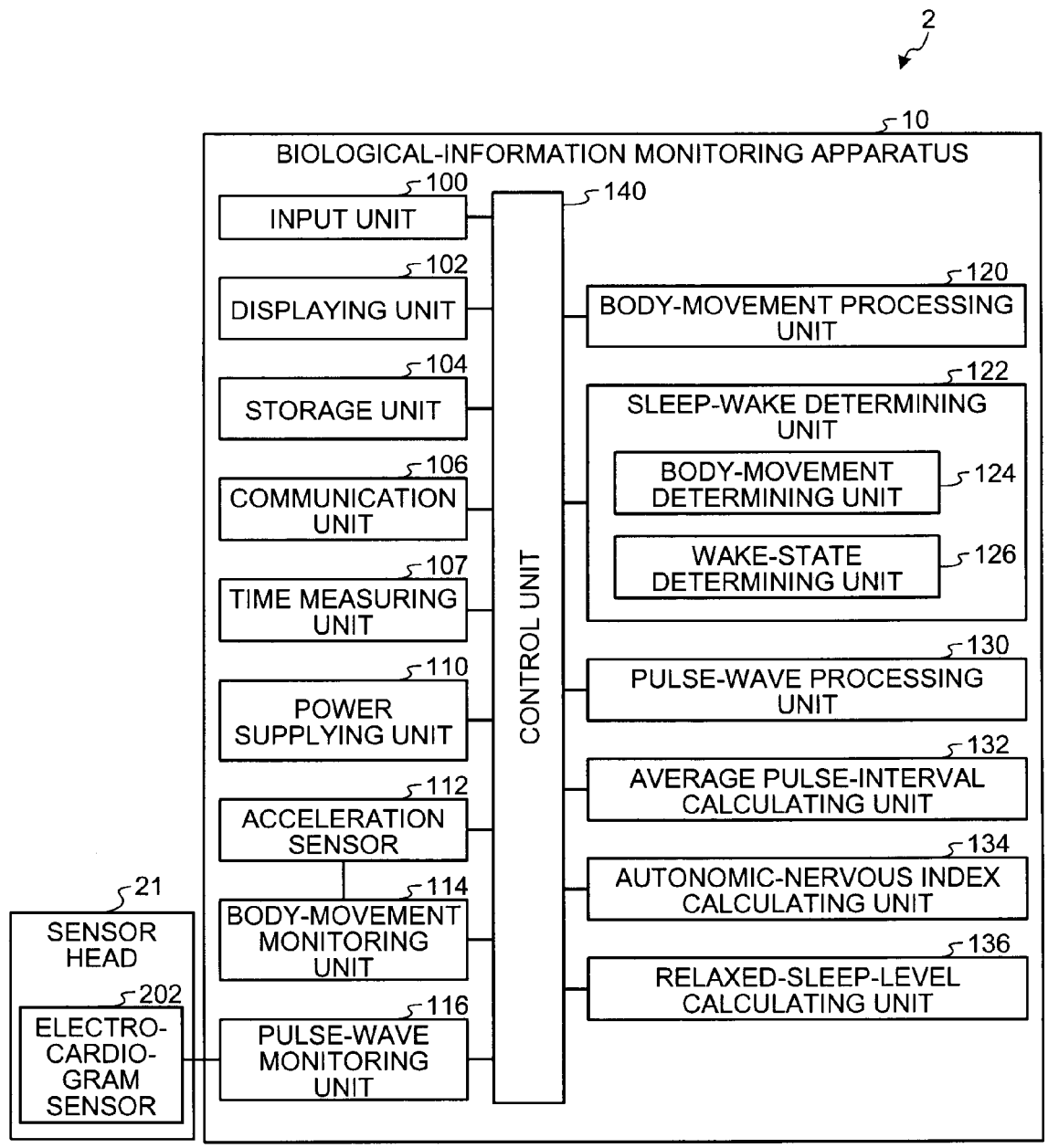
FIG. 11 is a block diagram of a biological-information monitoring system according to a first modification of the first embodiment.

A biological-information monitoring system 2 according to a first modification of the first embodiment is described below with reference to FIG. 11. Although the biological-information monitoring system 1 according to the first embodiment uses the heart rate variability based on pulse waves to obtain the autonomic index, the biological-information monitoring system 2 uses an electrocardiogram to obtain the heart rate variability. Similar results as the first embodiment can be obtained according to the first modification. The biological-information monitoring system 2 includes an electrocardiogram sensor 202 instead of the pulse-wave sensor 200 of the biological-information monitoring system 1. Cardiac potential signals are obtained with the electrocardiogram sensor 202 and pulsation for each beat is calculated. The other configurations and processes are identical to those of the biological-information monitoring system 1.

Figure 12:
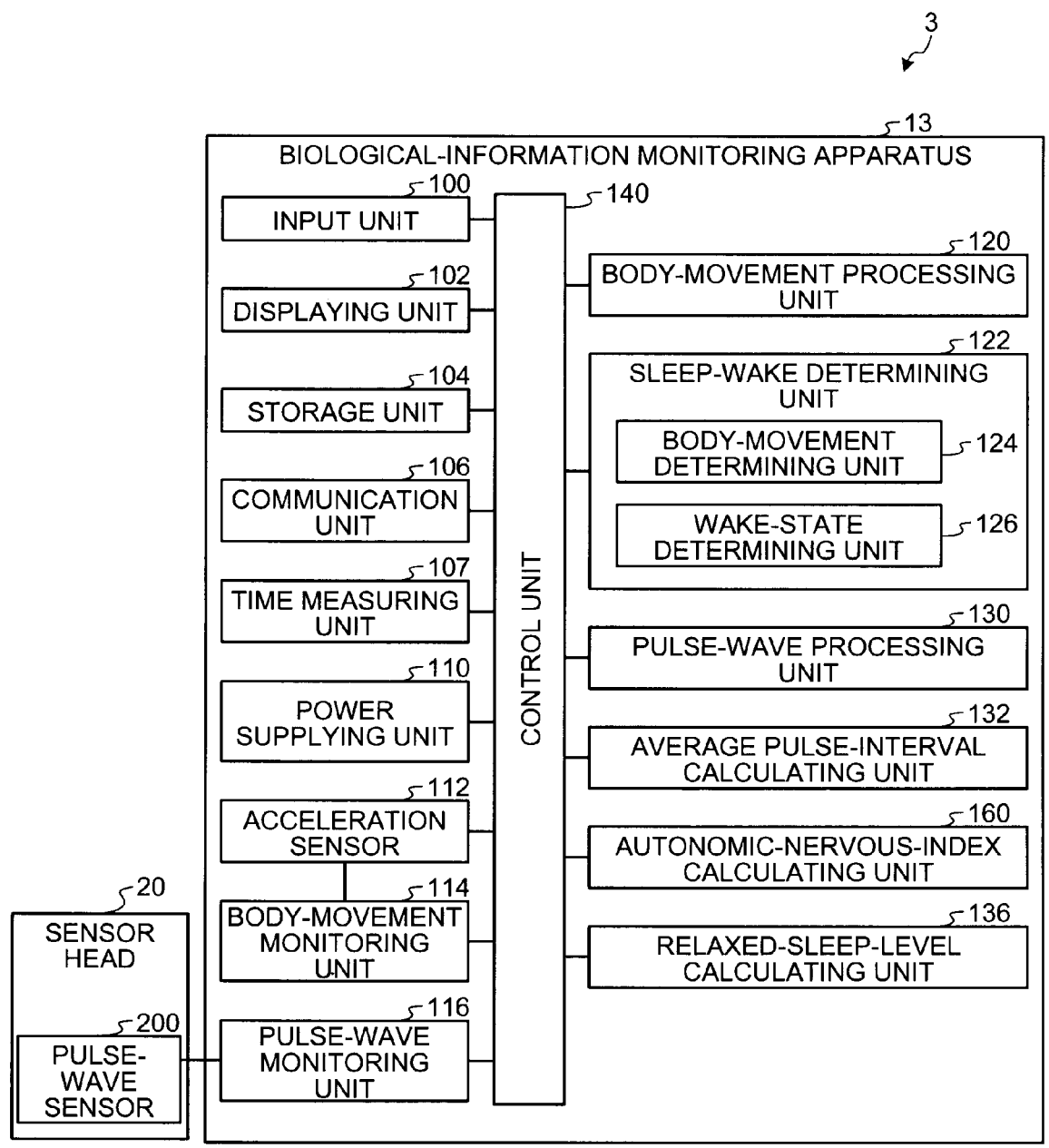
FIG. 12 is a block diagram of a biological-information monitoring system according to a second modification of the first embodiment.
Figure 13:
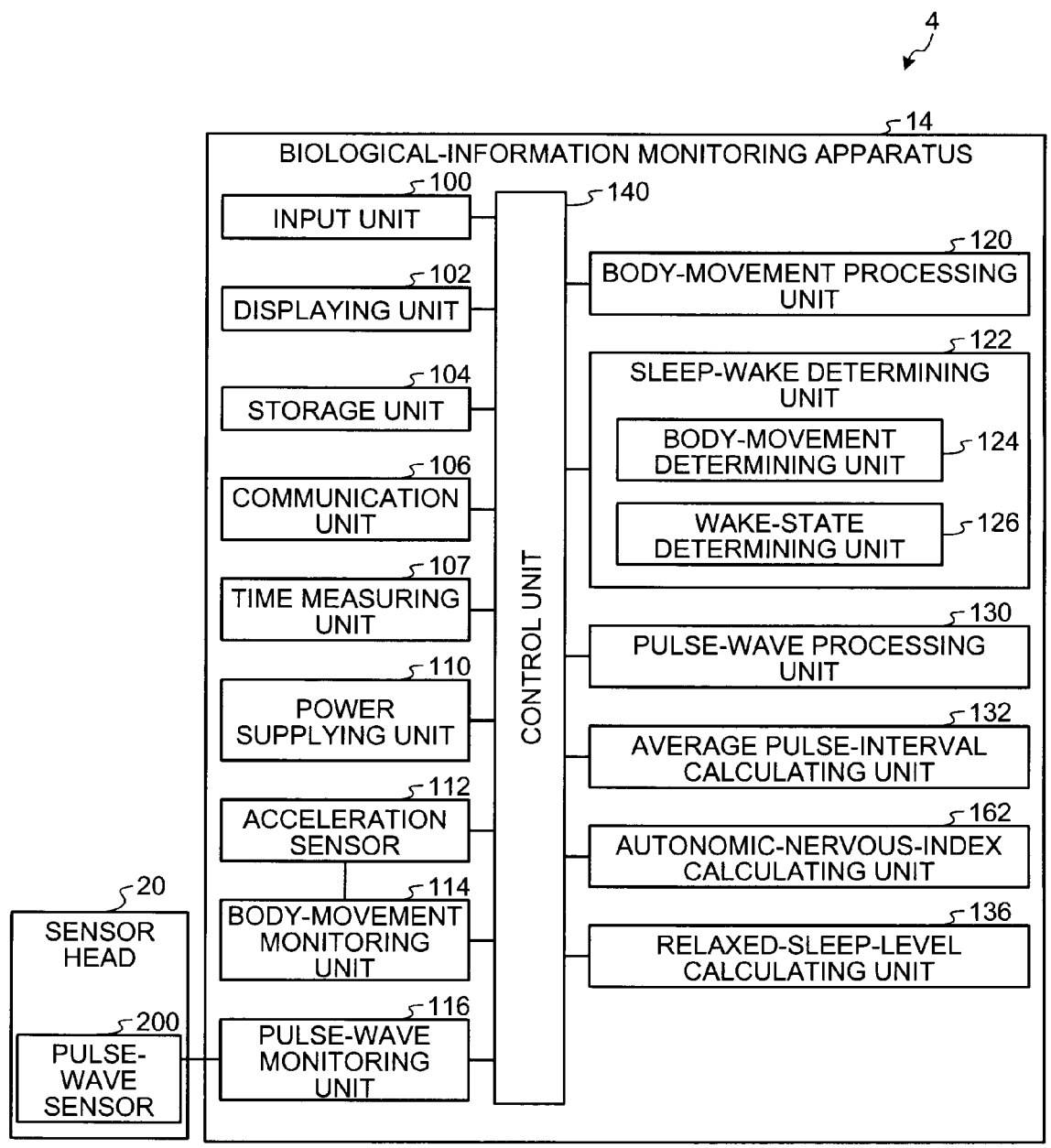
FIG. 13 is a block diagram of a biological-information monitoring system according to a third modification of the first embodiment.

A biological-information monitoring system 3 according to a second modification of the first embodiment is described below with reference to FIG. 12. The biological-information monitoring system 1 according to the first embodiment uses four points of pulse intervals right before a target pulse interval and calculates an aMSSD by averaging the four points. However, the biological-information monitoring system 3 includes an autonomic-nervous-index calculating unit 160 that uses pulse intervals adjacent to the target pulse interval. In other words, for example, four points in total including two points just before the target interval and two points just after the target interval, or a series of four points just after the target interval can be used.

When the method in the second modification is adopted, the aMSSD is calculated according to Equation 5.

$$aMSSD = \sum_{i=\frac{n}{2}-N}^{N} \left( \sum_{j=i-n/2+1}^{i+n/2} RR_{j-1}/n - RR_i \right)^2 / N \times 100 \quad (5)$$

A biological-information monitoring system 4 according to a third modification of the first embodiment is described below with reference to FIG. 14. The biological-information monitoring system 1 according to the first embodiment calculates an aMSSD based on a squared difference between an average pulse-interval data and the pulse interval RR5. However, the biological-information monitoring system 4 includes an autonomic-nervous-index calculating unit 162 that calculates an aMSSD based on an absolute value of the difference the average pulse interval and the pulse interval RR5.

Figure 14:
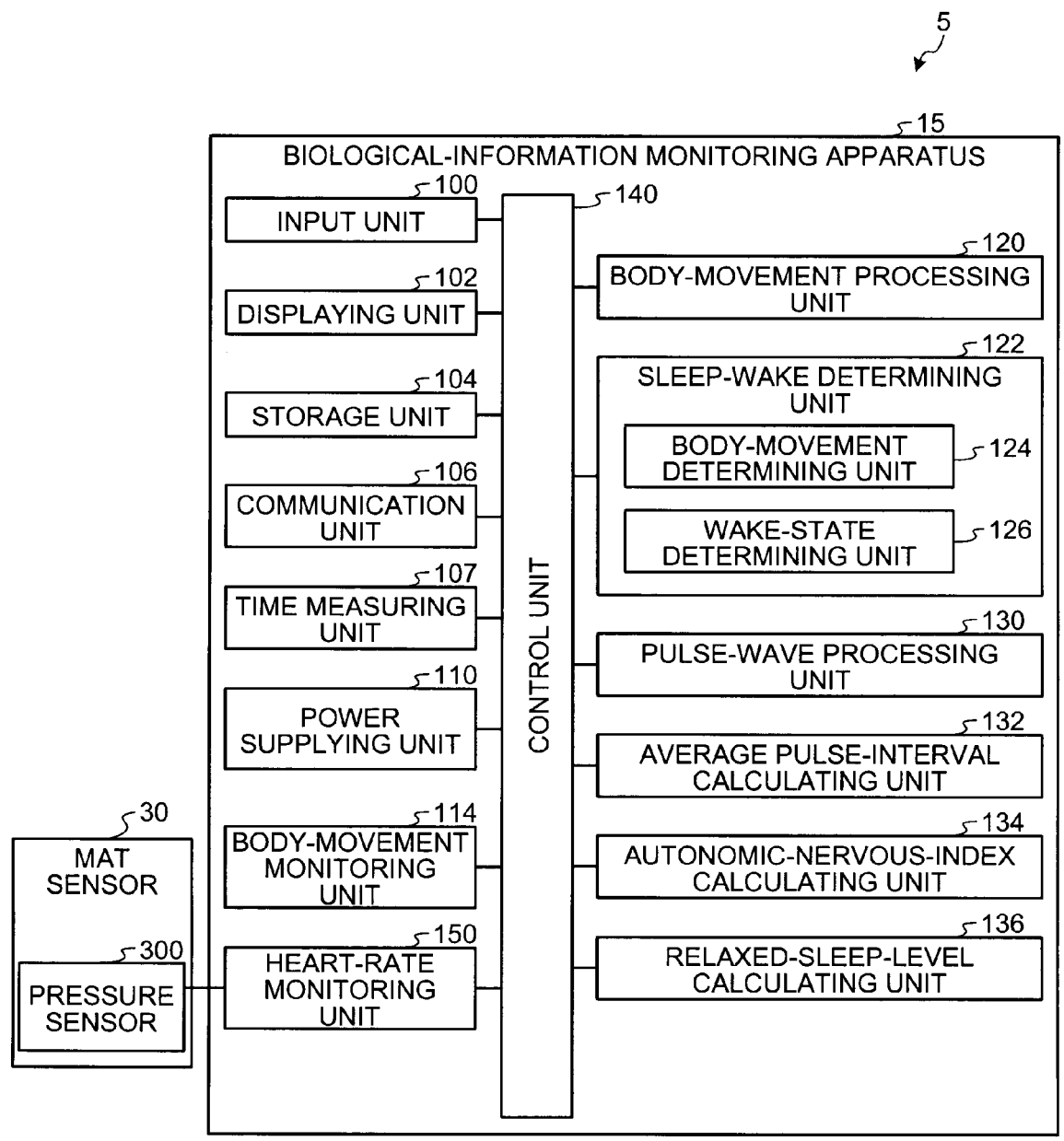
FIG. 14 is a block diagram of a biological-information monitoring system according to a second embodiment of the present invention.

As shown in FIG. 14, a biological-information monitoring system 5 according to a second embodiment of the present invention includes a mat sensor 30 instead of the sensor head 20 in the first embodiment, and a biological-information monitoring apparatus 15 instead of the biological-information monitoring apparatus 10 in the first embodiment. The mat sensor 30 includes a pressure sensor 300. The biological-information monitoring apparatus 15 includes a heart-rate monitoring unit 150 instead of the acceleration sensor 112 and the pulse-wave monitoring unit 116 of the biological-information monitoring apparatus 10 according to the first embodiment.

Figure 15:
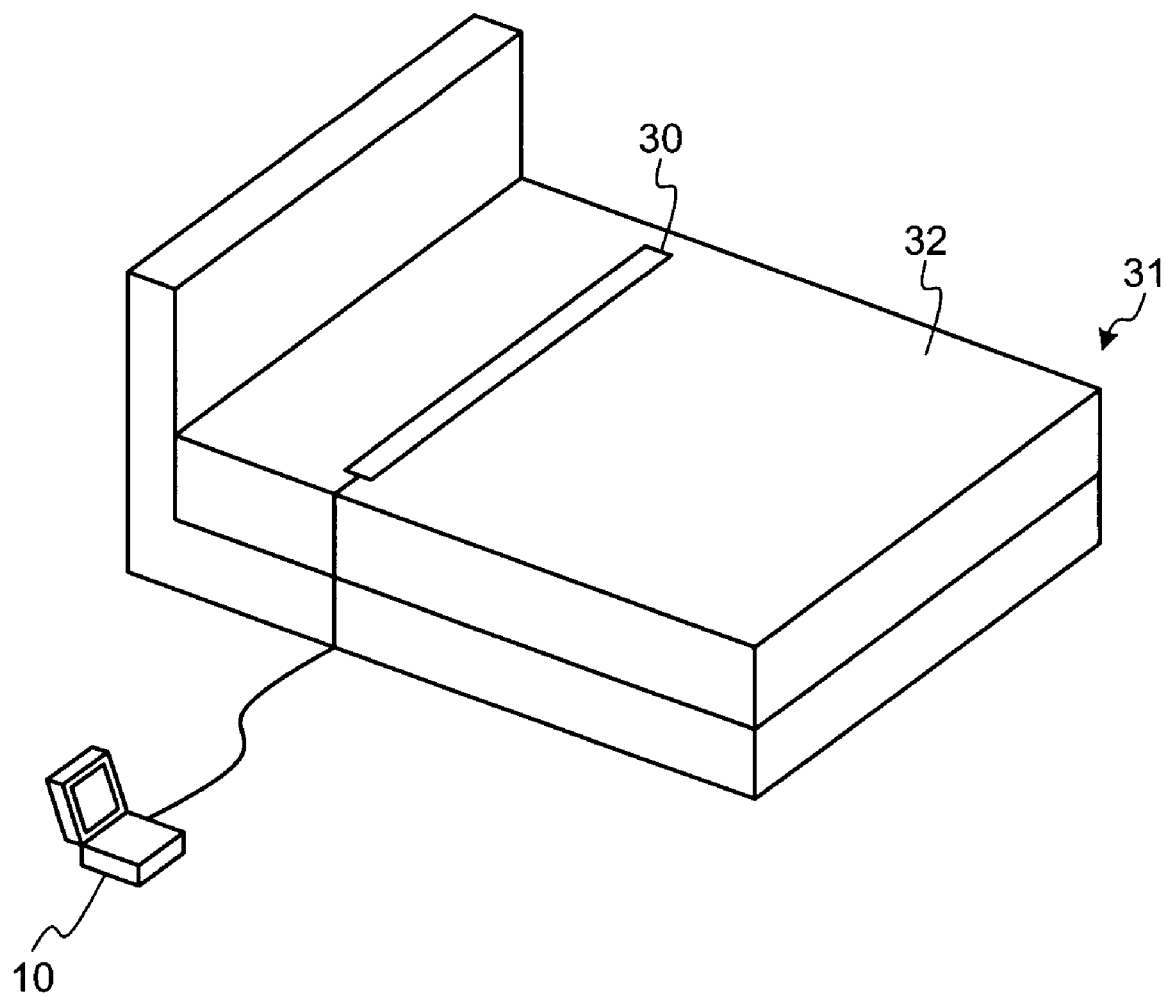
FIG. 15 is a schematic for explaining an arrangement of a mat sensor according to the second embodiment.

As shown in FIG. 15, the mat sensor 30 is laid on a surface of a mattress 32 on a bed 31 on which the target person sleeps. The mat sensor 30 detects presence or absence of the target person and body movements of the target person. The mat sensor 30 is laid on a position corresponding to the target person's chest or abdomen, and the pressure sensor 300 monitors vibrations due to the target person's movements. A heart rate and body movements are detected from monitored results.

The mat sensor 30 is made of a piezoelectric polymer material such as polyvinylidene fluoride. The mat sensor 30 is a strip of a piezoelectric element with flexible electrode films attached to both faces of a piezoelectric polymer film.

The body-movement monitoring unit 114 according to the second embodiment converts an output signal from the mat sensor 30 into digital data with the ADC by passing the signal through a filter and an amplifier. The suitable filter to a band for the body movements is used. The heart-rate monitoring unit 150 also converts an output signal from the mat sensor 30 into digital data with an ADC by passing the signal through a filter and an amplifier. The suitable filter to a band for heart rates is used.

Thus, the biological-information monitoring system 5 monitors the heartbeats instead of the pulse waves in the first embodiment. The monitored results are processed similar to those of the pulse waves in the first embodiment. The results of the heart rate and the pulse waves are practically identical with respect to data for the autonomic nervous index. The other configurations and processes of the biological-information monitoring system 5 are identical to those of the biological-information monitoring system 1.

Figure 16:
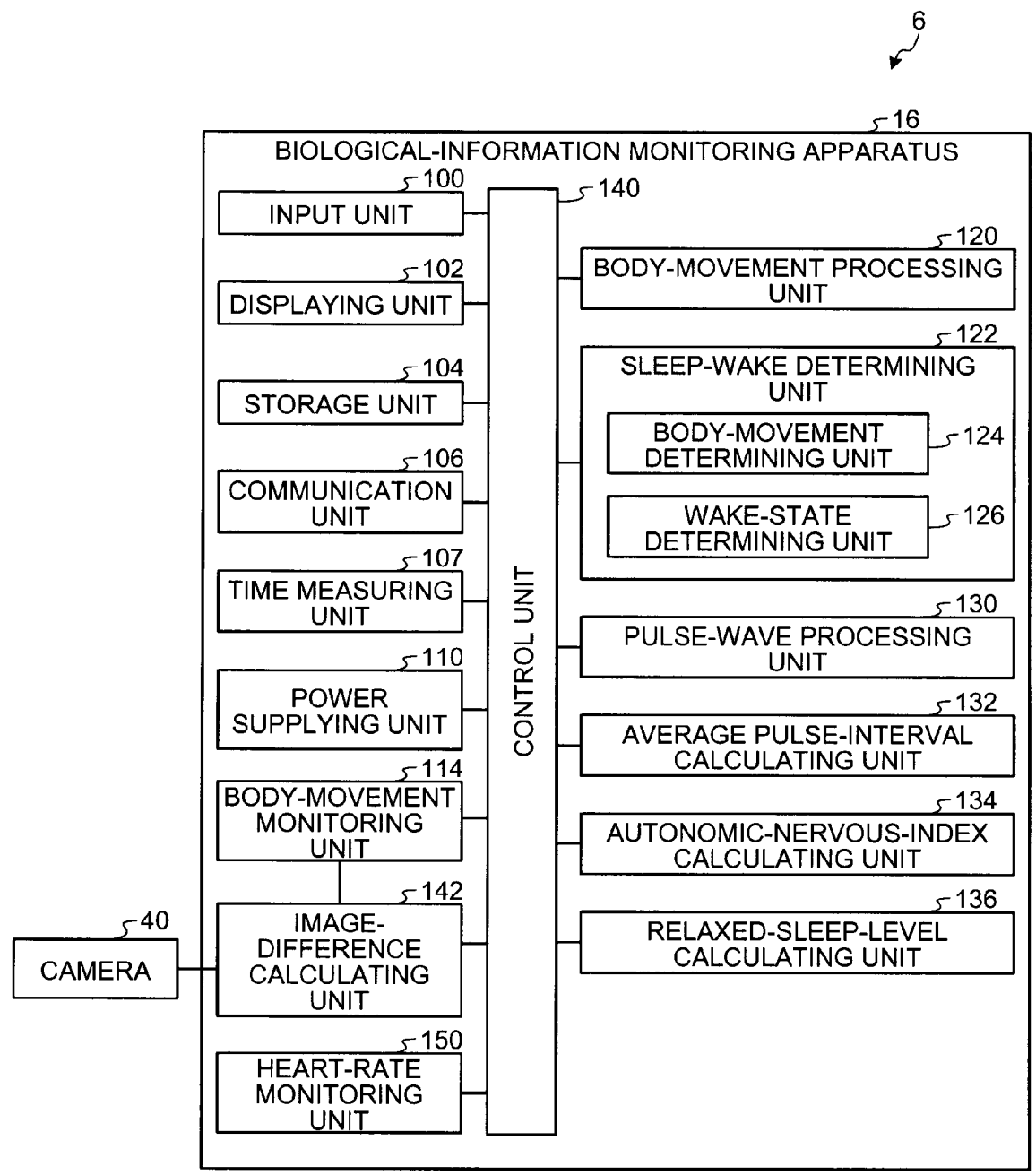
FIG. 16 is a block diagram of a biological-information monitoring system according to a third embodiment of the present invention.

As shown in FIG. 16, a biological-information monitoring system 6 according to a third embodiment of the present invention includes a camera 40 instead of the sensor head 20 in the first embodiment, and a biological-information monitoring apparatus 16 instead of the biological-information monitoring apparatus 10 in the first embodiment. The biological-information monitoring apparatus 16 includes an image-difference calculating unit 142 and the heart-rate monitoring unit 150 instead of the acceleration sensor 112 and the pulse-wave monitoring unit 116 of the biological-information monitoring apparatus 10.

Images of a blanket, which the target person puts on himself when he sleeps, are shot with the camera 40. The image-difference calculating unit 142 of the biological-information monitoring apparatus 16 obtains a time series of difference images shot with the camera 40. The blanket is slightly moved in synchronism with the target person's breathing and heartbeats, so that an amount of change in movements is obtained by calculating differences between frames in a time series and summing up the differences for each pixel. When a body movement occurs, an amount of change in the body movement can be obtained. The difference image contains a combination of movements such as breathing and body movements. The body-movement monitoring unit 114 according to the third embodiment separately extracts the body-movement data by filtering the difference images with the filter suitable to a band for body movements. Similarly, the heart-rate monitoring unit 150 separately extracts the heartbeat data by filtering the difference images with the filter suitable to a band for heartbeats.

The biological-information monitoring apparatus 16, like the biological-information monitoring apparatus 15, processes the heartbeat data for, for example, calculating the autonomic nervous index instead of the pulse-wave data. The other configurations and processes of the biological-information monitoring system 6 are identical to those of the biological-information monitoring systems according to other embodiments.

Figure 17:
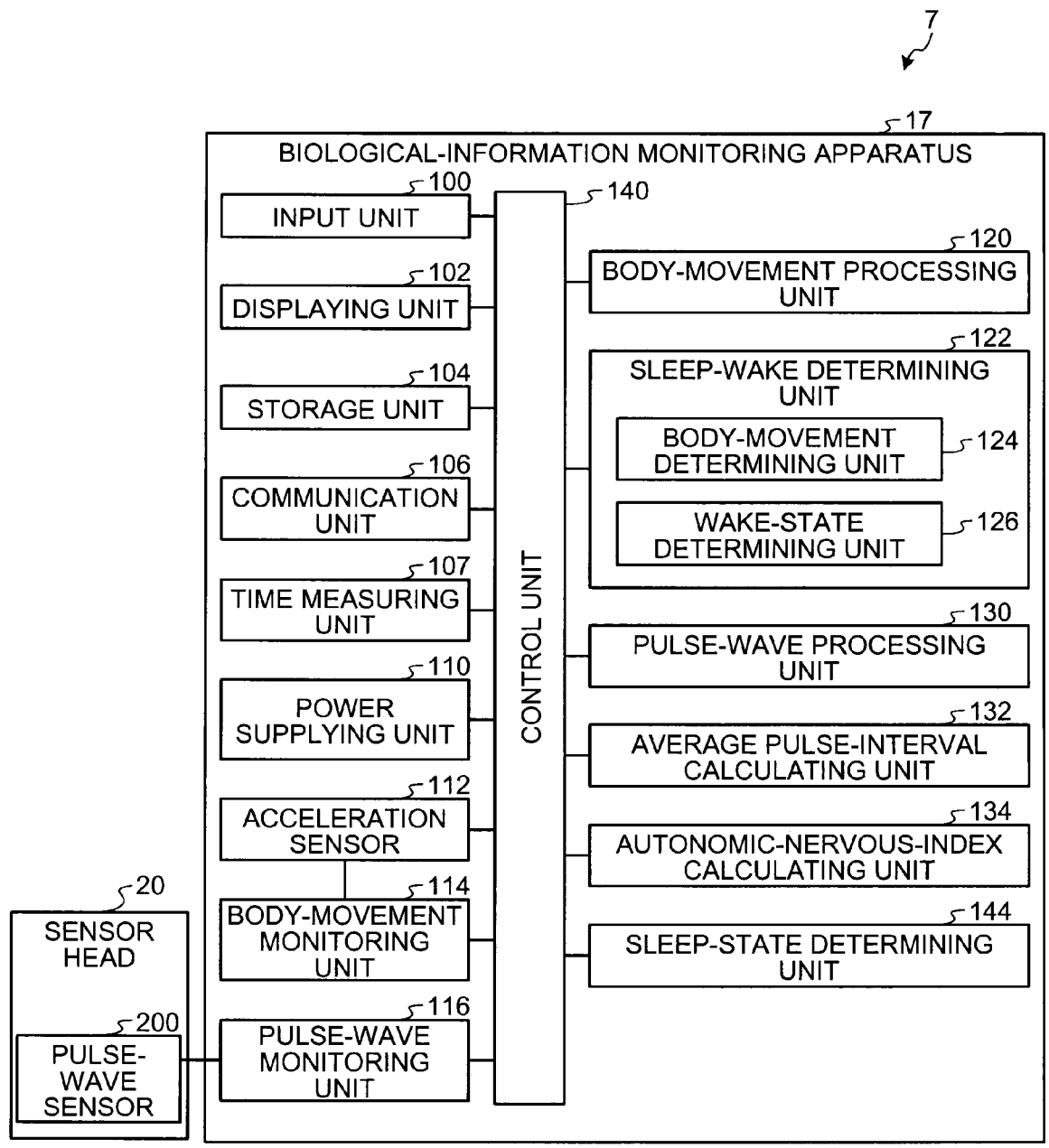
FIG. 17 is a block diagram of a biological-information monitoring system according to a fourth embodiment of the present invention.

As shown in FIG. 17, a biological-information monitoring system 7 according to a fourth embodiment of the present invention includes a sleep-state determining unit 144 instead of the relaxed-sleep-level calculating unit 136 in the first embodiment, and a biological-information monitoring apparatus 17 instead of the biological-information monitoring apparatus 10 in the first embodiment. The autonomic-nervous-index calculating unit 134 according to the fourth embodiment calculates, in addition to the aMSSD, dispersion of average pulse intervals. The data indicative of the dispersion is stored in the storage unit 104 as a sympathetic nervous index. More practically, the averages of pulse intervals each calculated when a beat of the pulse is detected are accumulated in the storage unit 104. A standard deviation of the averages of pulse intervals within a predetermined period (for example, 1 minute) is calculated. The standard deviation represents the dispersion of average pulse intervals. The dispersion of average pulse intervals is a sympathetic nervous index.

The sleep-state determining unit 144 determines a sleep state based on the sympathetic nervous index and the parasympathetic nervous index for one night calculated by the autonomic-nervous-index calculating unit 134. The sleep state can be any one of rapid eye movement sleep (REM sleep), light non-REM sleep, and deep non-REM sleep.

Figure 18:
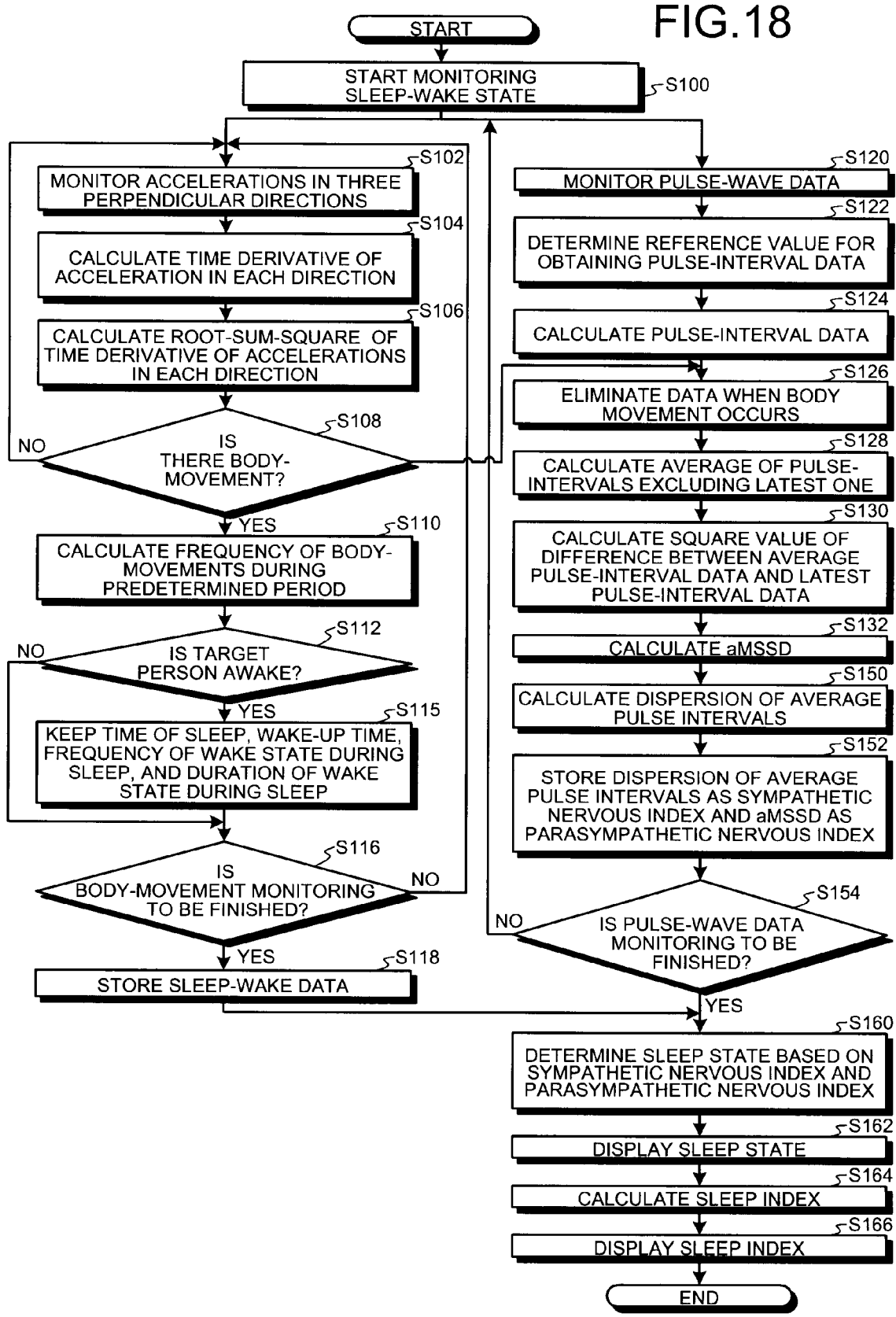
FIG. 18 is a flowchart for explaining operations performed by the biological-information monitoring apparatus shown in FIG. 17.

As shown in FIG. 18, when the body-movement monitoring is to be finished (Yes at step S116), the biological-information monitoring apparatus 17 causes the storage unit 104 to store data in the sleep or wake state, which represents results of the determination of whether the target person's wake or sleep state at a plurality of time points (step S118).

Furthermore, the aMSSD is calculated (step S132), and dispersion of average pulse intervals is calculated (step S150). The order in which the aMSSD is calculated and the dispersion of average pulse intervals is calculated can be changed from that shown in FIG. 18.

The dispersion of average pulse intervals and the aMSSD are stored in the storage unit 104 as a sympathetic nervous index and a parasympathetic nervous index, respectively (step S152). When the pulse-wave data monitoring is to be finished (step S154), the sleep-state determining unit 144 determines a sleep state of the target person based on the sympathetic nervous index and the parasympathetic nervous index (step S160). A result of determination of the sleep state is displayed on the displaying unit 102 (step S162). A sleep index is calculated (step S164), and the sleep index is displayed on the displaying unit 102 (step S166). At this time point, the operations performed by the biological-information monitoring apparatus 17 are finished.

Figure 19:
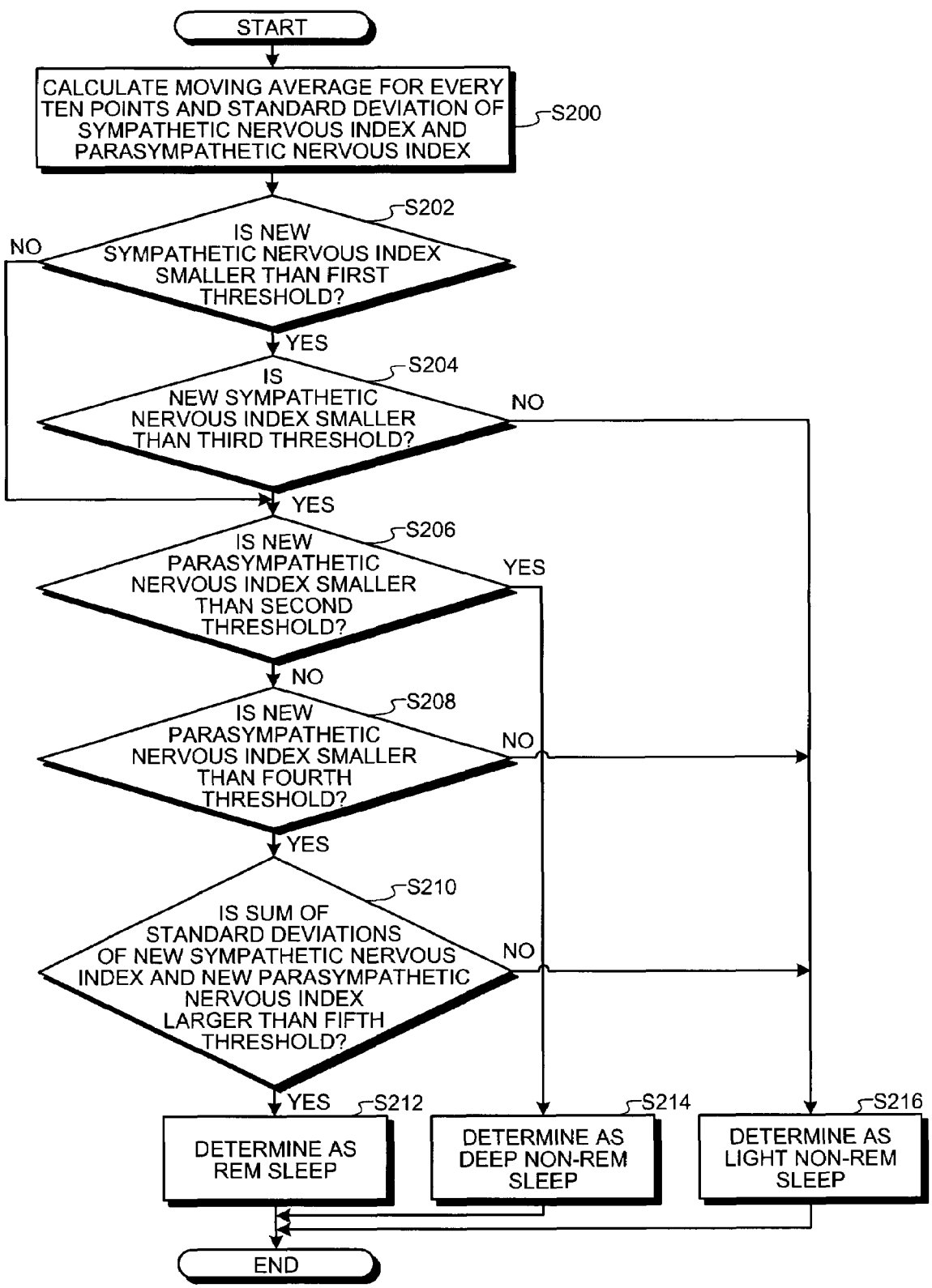
FIG. 19 is a flowchart for explaining detailed operations performed at step S160 shown in FIG. 18.

FIG. 19 is a detailed flowchart of the process for determining the sleep state performed at step S160 shown in FIG. 18. The sleep-state determining unit 144 first calculates standard deviations of the sympathetic nervous index and the parasympathetic nervous index. Next, the sympathetic nervous index is raised to the power of a moving average by ten points. The resulted value is regarded as a new sympathetic nervous index. Like the sympathetic nervous index, the parasympathetic nervous index is raised to the power of a moving average for every ten points. The resulted value is regarded as a new parasympathetic nervous index (step S200).

When the new sympathetic nervous index is smaller than a first threshold (Yes at step S202), the new sympathetic nervous index is smaller than a third threshold (Yes at step S204), the new parasympathetic-nervous index is not smaller than a second threshold (No at step S206), the new parasympathetic nervous index is smaller than a fourth threshold (Yes at step S208), and a sum of the standard deviation of the new sympathetic nervous index and the standard deviation of the new parasympathetic nervous index is larger than a fifth threshold (Yes at step S210), the sleep-state determining unit 144 determines that the sleep state of the target person is the REM sleep (step S212).

When the new parasympathetic nervous index is smaller than the second threshold (Yes at step S206), the sleep-state determining unit 144 determines that the sleep state of the target person is the deep non-REM sleep (step S214). When the new sympathetic nervous index is not smaller than the third threshold (No at step S204) the sleep-state determining unit 144 determines that the sleep state of the target person is the light non-REM sleep (step S216). When the new sympathetic nervous index is not smaller than the first threshold (No at step S202), the system control goes to step S206.

When the new parasympathetic nervous index is not smaller than the fourth threshold (No at step S208), or the sum of the standard deviation of the new sympathetic nervous index and the standard deviation of the new parasympathetic nervous index is not larger than the fifth threshold (No at step S210), the sleep-state determining unit 144 determines that the sleep state of the target person is light non-REM sleep (step S216).

The first to fifth thresholds can be set, for example, as described below. A new sympathetic nervous index, a new parasympathetic nervous index, and a sum of a standard deviation of the new sympathetic nervous index and a standard deviation of the new parasympathetic nervous index are calculated for the target person for one night. Two points with a high density are selected out of the distribution of each three indexes described above. A midpoint of the two points out of the new sympathetic nervous index represents the first and third thresholds; a midpoint of the two points out of the new parasympathetic nervous index represents the second and fourth thresholds; and a midpoint of the two points out of the sum represents the fifth threshold.

Figure 20:
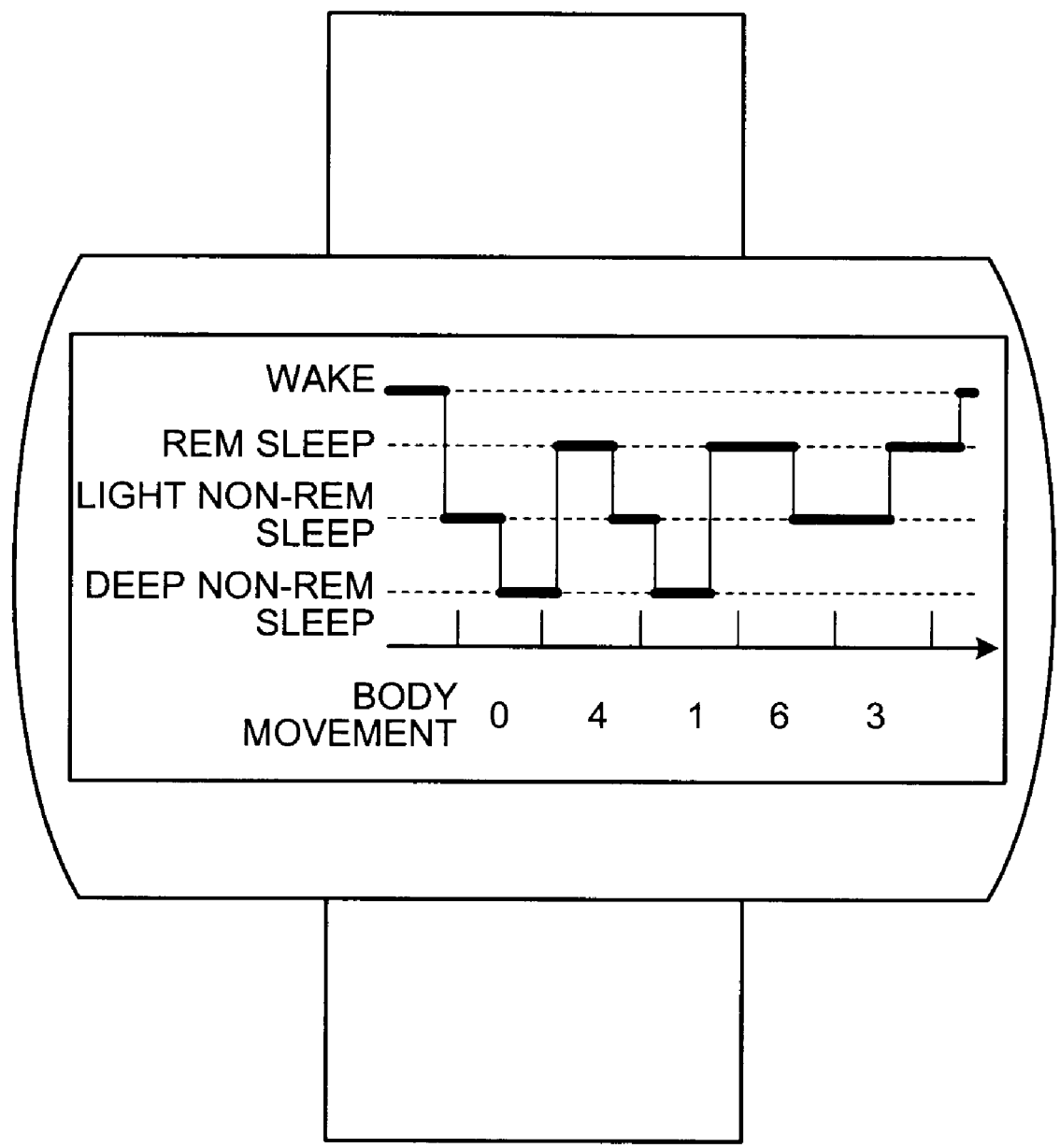
FIG. 20 is a schematic for explaining contents displayed on a display screen of a displaying unit.

The displaying unit 102 displays, at step S162, the graph shown in FIG. 20 that represents changes in the sleep state by hour on a display screen.

The other configurations and processes are identical to those of the biological-information monitoring systems according to the other embodiments.

Figure 21:
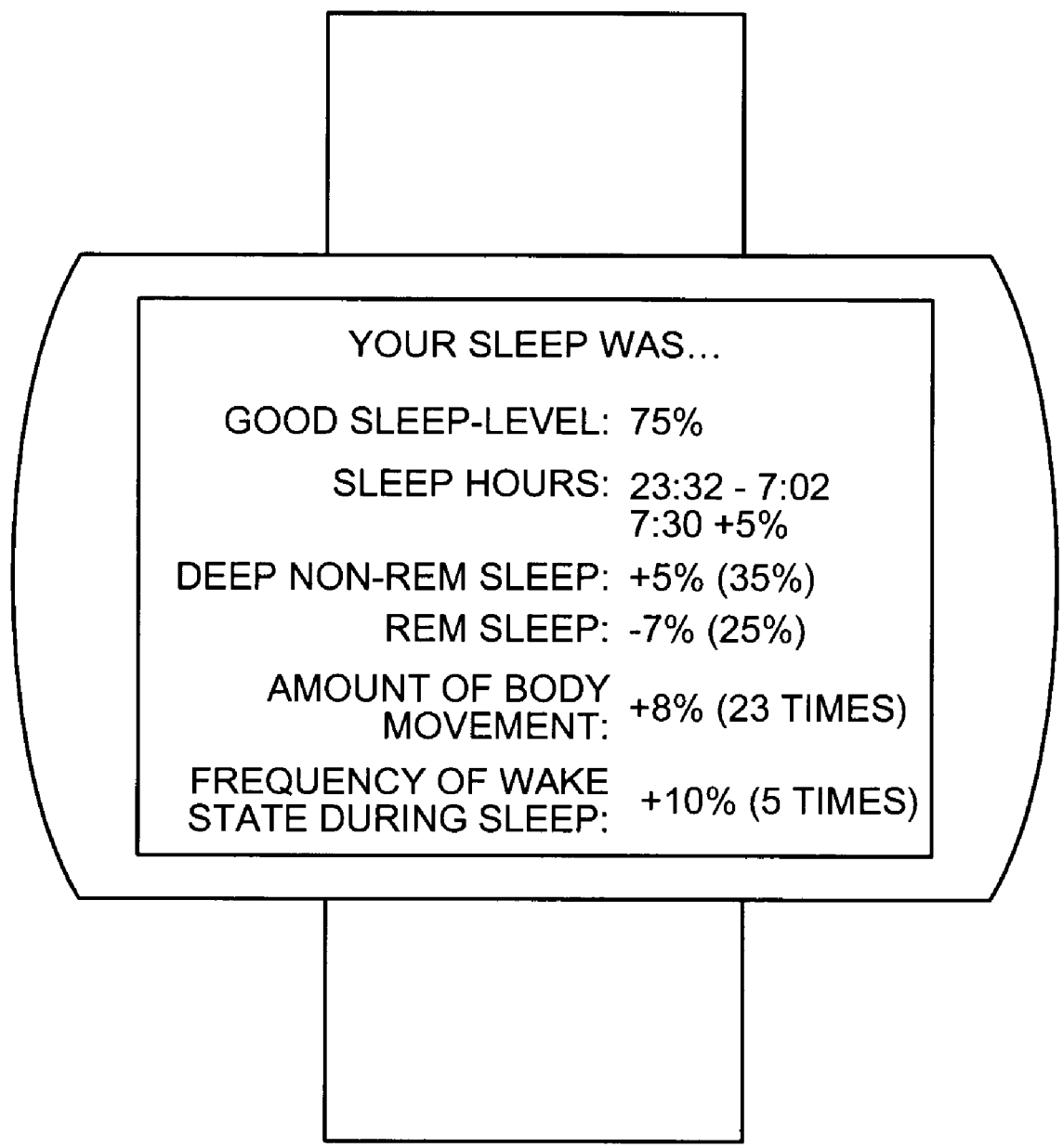
FIG. 21 is a schematic for explaining contents displayed on a display screen of a displaying unit according to a first modification of the fourth embodiment.

As shown in FIG. 21, indexes such as a sleeping hour, a ratio of each sleeping state, and the number of body movements can be displayed on the display screen of the displaying unit 102 instead of the graphical representation shown in FIG. 20.

Dispersion of pulse-wave amplitude can be used as a new sympathetic nervous index instead of the dispersion of the average pulse intervals.

Figure 22:
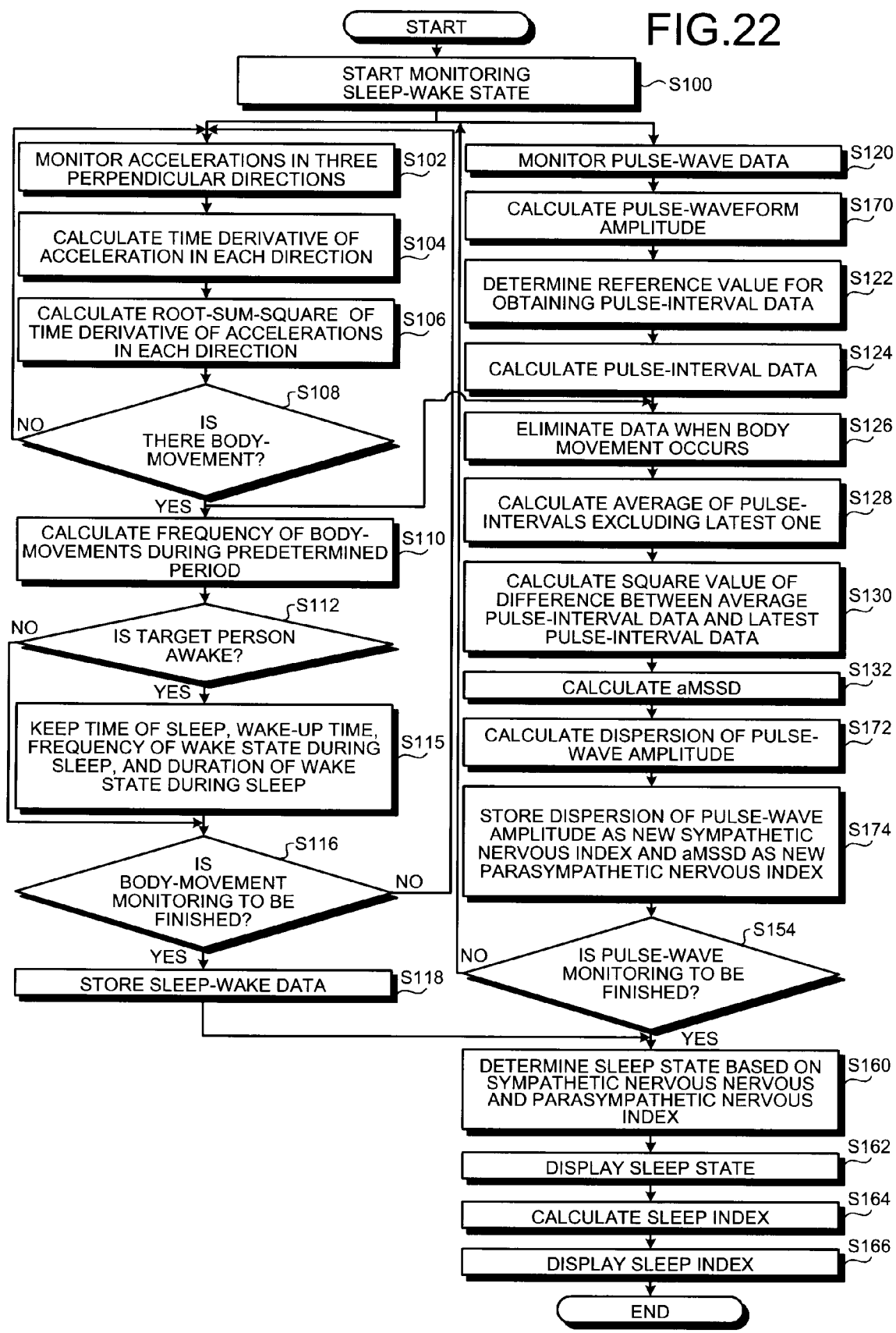
FIG. 22 is a flowchart for explaining operations according to a second modification of the fourth embodiment.

As shown in FIG. 22, when the dispersion of pulse-wave amplitude is employed, the pulse-wave sensor 200 starts monitoring the pulse wave data of the target person (step S120), pulse-waveform amplitude is calculated (step S170). Also, dispersion of pulse-wave amplitude is calculated instead of dispersion of average pulse intervals (step S172). More specifically, the dispersion of pulse-wave amplitude represents a standard deviation of pulse-wave amplifier within a predetermined period, for example, 1 minute. The dispersion of pulse-wave amplitude and the aMSSD are stored in the storage unit 104 as a new sympathetic nervous index and a new parasympathetic nervous index, respectively (step S174).

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A biological-information monitoring apparatus comprising:
   a detecting unit that detects pulse intervals of a target person;
   a first calculating unit that calculates an average of the pulse intervals within a first period, wherein the first period is determined based on a target pulse interval; and
   a second calculating unit that calculates a parasympathetic nervous index based on a difference between the average pulse interval and the target pulse interval.

2. The apparatus according to claim 1, wherein the second calculating unit calculates the parasympathetic nervous index based on any one of
   an average of square values of differences between the average pulse interval and the target pulse interval within a second period, and
   an average of absolute values of differences between the average pulse interval and the target pulse interval within a second period.

3. The apparatus according to claim 1, wherein the first calculating unit averages the pulse intervals in a series monitored within the first period immediately before the target pulse interval.

4. The apparatus according to claim 1, wherein the first calculating unit averages the pulse intervals in a series monitored within the first period immediately after the target pulse interval.

5. The apparatus according to claim 1, wherein the first calculating unit sets the first period based on a breathing cycle of the target person.

6. The apparatus according to claim 1, further comprising a determining unit that determines, based on the parasympathetic nervous index, transitions of a sleep state of the target person.

7. The apparatus according to claim 1, further comprising a monitoring unit that monitors a cardiac potential of the target person, wherein
the detecting unit detects the pulse intervals based on the cardiac potential.

8. The apparatus according to claim 1, further comprising a monitoring unit that monitors a pressure due to a body of the target person, wherein
the detecting unit detects the pulse intervals based on the pressure.

9. The apparatus according to claim 1, further comprising an imaging unit that captures images of the target person at different time points, wherein
the detecting unit detects the pulse intervals based on changes in the images.

10. A computer-implemented method of monitoring and processing biological information of a target person, the method comprising:
detecting pulse intervals of the target person based on a pulse sensor;
calculating an average pulse interval that is an average of the pulse intervals within a first period, wherein the first period is decided based on a target pulse interval; and
calculating a parasympathetic nervous index based on a difference between the average pulse interval and the target pulse interval.

11. A computer product including a recording medium readable by a computer and containing a plurality of instructions executable on the computer for monitoring and processing of biological information, the instructions causing the computer to execute:
detecting pulse intervals of a target person;
calculating an average pulse interval that is an average of the pulse intervals within a first period, wherein the first period is decided based on a target pulse interval; and
calculating a parasympathetic nervous index based on a difference between the average pulse interval and the target pulse interval.

* * * * *